US012745939B2

(12) United States Patent
Callens et al.

(10) Patent No.: US 12,745,939 B2
(45) Date of Patent: Sep. 29, 2026

(54) MEASUREMENT STATION WITH HANDLE

(71) Applicant: Withings, Issy les Moulineaux (FR)

(72) Inventors: Victorine Callens, Issy les Moulineaux (FR); Thomas Droze, Issy les Moulineaux (FR); Victor Geffraye, Issy les Moulineaux (FR); Antoine Merlot, Issy les Moulineaux (FR); Arthur Richard, Issy les Moulineaux (FR); Jean-Louis Wang, Issy les Moulineaux (FR)

(73) Assignee: WITHINGS, Issy les Moulineaux (FR)

( * ) Notice: Subject to any disclaimer, the term of this patent is extended or adjusted under 35 U.S.C. 154(b) by 569 days.

(21) Appl. No.: 18/087,333

(22) Filed: Dec. 22, 2022

(65) Prior Publication Data

US 2023/0210429 A1 Jul. 6, 2023

(30) Foreign Application Priority Data

Dec. 31, 2021 (FR) ...................................... 2114742

(51) Int. Cl.

| | |
|---|---|
| ***G01G 21/28*** | (2006.01) |
| ***A61B 5/0531*** | (2021.01) |
| ***A61B 5/26*** | (2021.01) |
| ***A61B 5/282*** | (2021.01) |
| ***G01G 19/50*** | (2006.01) |

(52) U.S. Cl.

CPC .............. *A61B 5/26* (2021.01); *A61B 5/0531* (2013.01); *A61B 5/282* (2021.01); *G01G 19/50* (2013.01)

(58) Field of Classification Search

CPC ..... A61B 5/0205; A61B 5/053; A61B 5/0537; A61B 5/26; A61B 2560/0443; A61B 2560/045; A61B 2560/0456; B66D 1/36; B66D 1/39; G01G 19/00; G01G 21/00

See application file for complete search history.

(56) References Cited

U.S. PATENT DOCUMENTS 4,087,060 A * 5/1978 Laky ........................ B66D 1/39 242/484
7,753,344 B1 * 7/2010 Moretz .................. E21B 19/22 254/331
8,494,609 B2 * 7/2013 Karo .................... A61B 5/4872 600/382

(Continued)

FOREIGN PATENT DOCUMENTS

CN 204909451 U 12/2015
CN 211534389 U 9/2020

(Continued)

OTHER PUBLICATIONS

English translation of JP2010057540.*

(Continued)

*Primary Examiner* — Allen Porter
(74) *Attorney, Agent, or Firm* — CUSHMAN PARTNERS, LLC

(57) ABSTRACT

A measurement station includes a base including a measurement plate having an upper surface adapted to receive a user's feet, a handle support, mounted on the upper surface of the measurement plate, a handle adapted to receive a user's hands, the handle being configured to be received on the handle support.

20 Claims, 18 Drawing Sheets

(56) References Cited

U.S. PATENT DOCUMENTS

| | | | | |
|---|---|---|---|---|
| 2013/0158364 | A1* | 6/2013 | Hayn | A61B 5/0205 600/301 |
| 2014/0212850 | A1* | 7/2014 | Shimizu | G01G 19/50 434/127 |
| 2015/0359492 | A1* | 12/2015 | Giovangrandi | G01G 19/50 600/481 |

FOREIGN PATENT DOCUMENTS

| | | | |
|---|---|---|---|
| CN | 112022102 | A | 12/2020 |
| EP | 1 700 565 | A1 | 9/2006 |
| EP | 3 087 914 | A1 | 11/2016 |
| EP | 3 095 380 | A2 | 11/2016 |
| JP | 2003-299628 | A | 10/2003 |
| JP | 2010-057540 | A | 3/2010 |
| WO | WO 2010/122252 | | 10/2010 |
| WO | WO 2014/013208 | A1 | 1/2014 |
| WO | WO 2021/082876 | A1 | 5/2021 |
| WO | WO 2021/164561 | A1 | 8/2021 |
| WO | WO 2021/209720 | A1 | 10/2021 |

OTHER PUBLICATIONS

English translation of WO 2021164561.*
Search Report as issued in French Patent Application No. FR2114742, dated Sep. 21, 2022.

* cited by examiner

MEASUREMENT STATION WITH HANDLE

CROSS-REFERENCE TO RELATED APPLICATIONS

This application claims priority to French Patent Application No. 2114742, filed Dec. 31, 2021, the entire content of which is incorporated herein by reference in its entirety.

FIELD

The present description relates to the monitoring of a user's health and more specifically to measurement stations for implementing one or more measurements of biometric signals (or physiological parameters) of a user.

BACKGROUND

Document WO2010/122252, of 2010, discloses a connected scale with weight and bioimpedance measurement. Documents EP3087914 and EP3095380, from 2015, meanwhile, disclose a connected scale for obtaining information on the user's cardiovascular status, including a PTT ("pulse transit time") measurement using a BCG and an IPG.

Document CN211534389 discloses a balance with handle for performing segmental bioimpedance. Document WO2021/164561 discloses a balance with a handle for performing an ECG.

SUMMARY

An aspect of the present description aims to provide a measurement station that allows different measurements of biometric signals to be obtained with increased quality.

The invention is defined in the claims.

In an embodiment, the present description presents a measurement station comprising:

- a base including:
  - a measurement plate with an upper surface suitable for receiving the feet of a user,
  - a handle support, mounted on the upper surface of the measurement plate,
- a handle adapted to receive a user's hands, the handle being configured to be received on the handle support.

In an aspect of the invention, at least one of the following data is determined by the measurement station of the present application: weight or mass, electrocardiogram (ECG), impedance measurement (impedance analysis of the human body), including impedance-plethysmogram (IPG), impedance-cardiogram (ICG) and bioimpedance analysis (BIA), for the mass of fat, water, muscle, etc.), photoplethysmogram (PPG), ballistocardiogram (BCG), electrochemical skin conductance analysis ("ESC analysis" or simply "ESC" in the present description) and assessment of sweat function (sometimes referred to as "sudogram" in the present application), heart rate ("HR"), pulse wave velocity ("PWV"), etc.

The handle support may have a portion that defines a cradle. The cradle may have a shape complementary to that of the handle.

In an embodiment, the measurement station comprises a cable connecting the handle to the base. The cable includes electrical wiring for carrying electrical signals.

In an embodiment, the measurement plate comprises a plate through hole through which the cable connecting the handle to the base passes. The plate through-hole may be cylindrical and elongated, in particular in a direction orthogonal to the measurement plate.

In an embodiment, the handle support comprises a support through hole through which the cable passes. The support through-hole may be cylindrical and elongated, in particular along a direction orthogonal to the measurement plate.

In an embodiment, the plate through-hole and the surface through-hole face each other.

In an embodiment, the cable extends orthogonally from a surface of the handle so that it may be inserted into the through holes when the handle is positioned in the handle support.

In an embodiment, the support through hole has a chamfer to eliminate the sharp edge.

In an embodiment, the base comprises a reel capable of winding and unwinding the cable.

In an embodiment, the base includes a roller configured to facilitate a change in direction of the cable during winding and unwinding of the cable.

In an embodiment, the grinding station comprises a second roller configured to channel the movement of the cable, the two rollers being on opposite sides of the cable.

In an embodiment, the station comprises a support plate disposed within the base and on which the roller is mounted.

In an embodiment, in the stowed position, the cable is concealed by the handle and handle support.

In an embodiment, the handle support forms a cradle configured to receive the handle, in particular a cradle of complementary shape to the handle.

In one embodiment, the through hole of the handle support is positioned at the bottom of the cradle.

In an embodiment, the handle support extends in a transverse direction along the width of the base.

In an embodiment, the cradle extends over an area, in a cross-section of the handle support, of less than 90° on either side from a bottom of the cradle.

In one embodiment, the measurement station includes a magnetic fastener in the handle and handle support to help hold the handle in the handle support.

In an embodiment, the handle extends between two ends and comprises a plurality of electrodes arranged in sequence between the two ends. The handle may extend in a longitudinal direction or have a curved shape. The electrodes are spaced apart to insulate them from each other.

In an embodiment, the electrodes extend in a cross-section over at most an outer surface of the handle between −45° and +90°, where 0° is defined by an insertion position of the cable in the handle, and the range between 0° and +180° is defined as facing a front edge of the measurement station.

In an embodiment, the cradle extends over a surface whose angle in a cross-section of the handle support is at least equal to that of the electrodes in the negative angle direction.

In an embodiment, the measurement plate is flat, especially an upper face of the measurement plate is flat, and more particularly the portion of the upper face where the handle support is mounted is flat.

In an embodiment, the measurement plate is made of glass.

In an embodiment, the handle is configured to allow acquisition of an electrocardiogram (ECG) and impedance analysis (BIA, IPG).

The present description also presents, in an embodiment, a measurement station comprising:

a base comprising a measurement plate having an upper surface adapted to receive the feet of a user, a handle suitable for receiving the hands of a user, the handle extending between two ends and comprising a plurality of electrodes arranged in succession between the two ends, in particular with a spacing between them.

The measurement station may include a cable connecting the handle to the base,

In an embodiment, the electrodes extend in a cross-section over at most an outer surface of the handle between −45° and +90°, where 0° is defined by an insertion position of the cable in the handle, the range between 0 and +180° is defined as facing a front edge of the measurement station, the range between 0 and −180° is defined as facing a rear edge of the measurement station (when the handle is in a stowed position).

In an embodiment, in a cross section of the handle that includes an electrode, the angle defined by the barycenter of the external surface and the end of the electrodes is between −45° and +90° (in particular −30° and +80°), with 0° being the angle defined by the point on the outer surface which is closest to the measurement plate when the handle is in the stowed position, positive angles (0° to +180°) being defined from 0° on the leading edge side and negative angles (0° to −180°) being defined from 0° on the trailing edge side. In a cross section including the cable, the cable entry point is at 0°.

The present description also presents, in an embodiment, a measurement station comprising:

a base comprising a measurement plate having a top face adapted to receive a user's feet, a handle adapted to receive a user's hands, the handle comprising a plurality of electrodes In an embodiment, each electrode extends in a cross-section over at most one outer surface of the handle between −45° and +90°, where 0° is defined by the position of insertion of a cable into the handle, the range between 0° and +180° is defined as facing a leading edge of the measurement station, the range between 0° and −180° is defined as facing a trailing edge of the measurement station (when the handle is in a stowed position in a handle support).

In an embodiment, in a cross-section of the handle which includes an electrode, the angle defined by the barycenter of the external surface and the end of the electrodes is between −45° and +90° (in particular −30° and +80°), with 0° being the angle defined by the point on the outer surface which is closest to the measurement plate when the handle is in the stowed position, positive angles (0° to +180°) being defined from 0° on the leading edge side and negative angles (0° to −180°) being defined from 0° on the trailing edge side.

In an embodiment, the measurement station comprises a cable connecting the handle to the base; in a cross-section of the handle including the point of entry of the cable into the handle, said point of entry of the cable is at 0°.

In an embodiment, the measurement station includes a handle support configured to receive the handle. In particular, the handle support may have a portion that defines a cradle. The cradle may have a shape complementary to the handle.

In an embodiment, the cradle extends over a surface whose angle in a cross-section is at least equal to that of the electrodes in the negative angle direction when the handle is in a stowed position on the handle support.

The measurement station may include the other features described above.

DESCRIPTION OF THE FIGURES

The following figures illustrate the elements described in this description.

DETAILED DESCRIPTION

Figure 1:
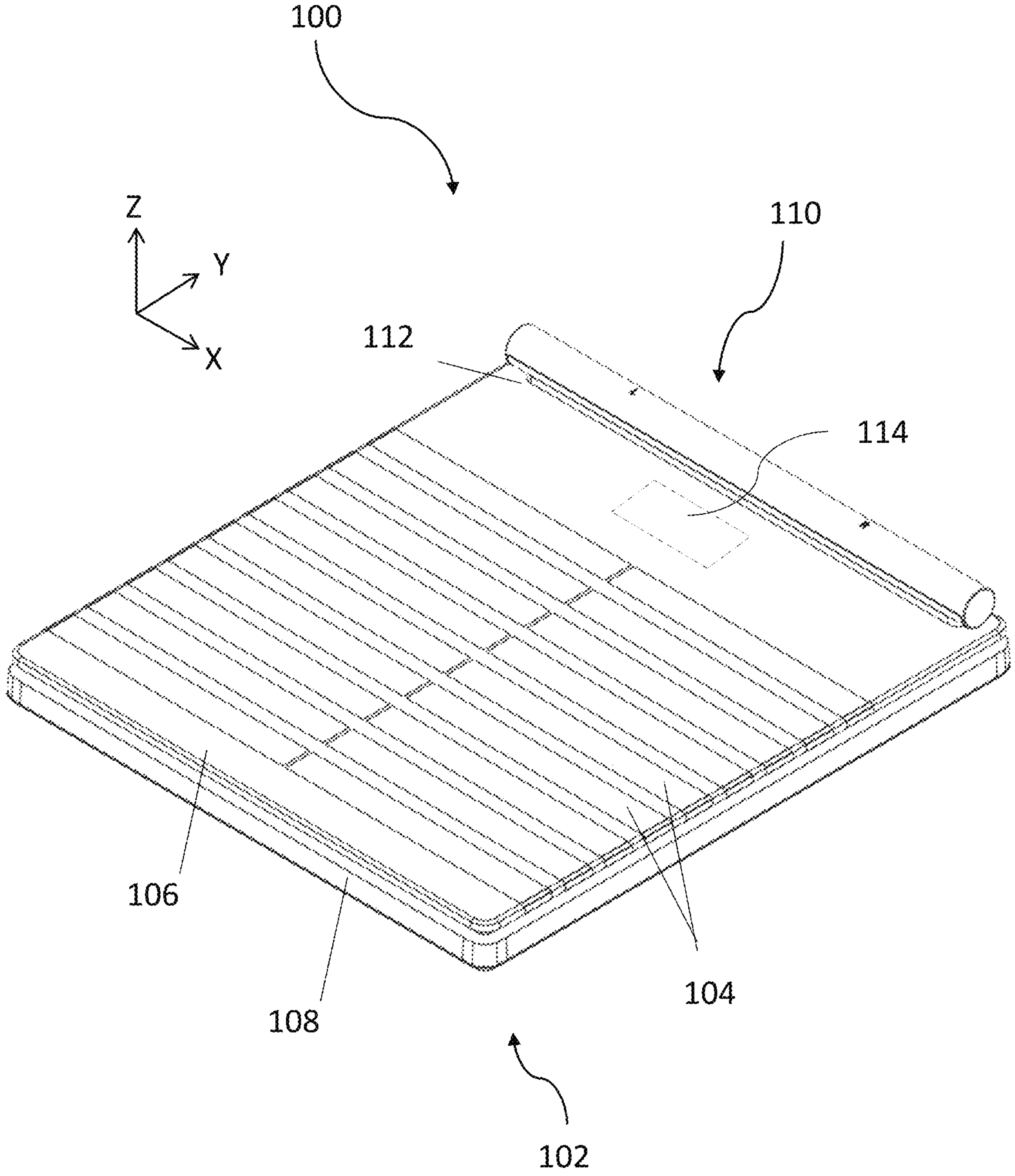
FIG. 1 shows a three-dimensional view of a measurement station with a handle, according to an embodiment.

FIGS. 1 to 4 illustrate an embodiment of a measurement station 100 according to at least one embodiment of the present description. The measurement station 100 is primarily in the form of a base 102 on which a user may place his or her feet, for example flat. The user may be on the measurement station or sitting on a chair. In the normal position of use, the user's feet lie flat on the measurement station 100. The thickness of the base 102 is, for example, less than 10 cm, or even 6 cm. The measurement station 100 includes one or more sensors 104 suitable for measuring physiological information of a user.

In an embodiment, some sensors 104 (e.g., electrodes) are mounted on a substrate 106 of the base 102, the substrate being configured to receive a user's feet. The substrate may be a rigid plate, as shown in the figures, and referred to as a measurement plate 106. The measurement plate 106 defines a plane parallel to an XY plane. The measurement plate 106 may be made of glass. Nevertheless, the substrate may be deformable under the weight of the user. The substrate 106 may be mounted on a base frame 108, such as a rigid base, or legs (not shown). In the case of a base 102 functioning as a bathroom scale, sensors are positioned between the substrate 106 and the base frame108 (so-called “sandwich” architecture) or between the substrate 106 and the feet (so-called “foot” architecture). The sensors may be load cells (typically four) that provide a weight, and thus a mass of a user. The base frame108 may be made of metal (aluminum, steel, etc.) or plastic.

Figure 2:
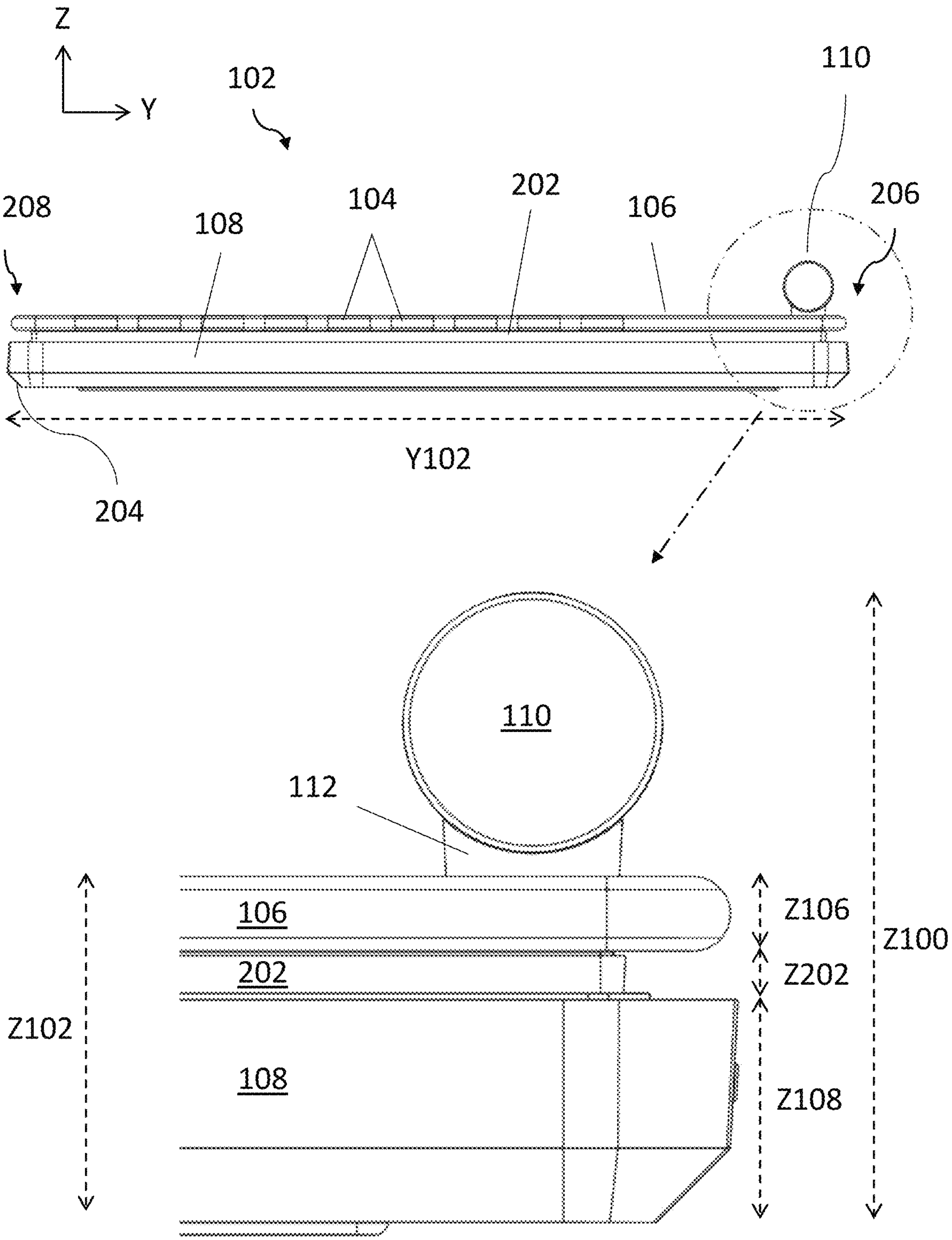
FIG. 2 shows a side view of the station of FIG. 1.

As seen in FIG. 2, the measurement station 100 further comprises a support plate 202, which may be integral with the measurement plate 106. The support plate 202 is designed to receive part of the electronics of the measurement station 100, in particular via a printed circuit board (“PCB”) mounted on the support plate 202. The support plate 202 is thus positioned between the base 108 and the measurement plate 106.

In an architecture with legs, two groups are defined that move in relation to each other: the legs on the one hand (fixed group), and everything else on the other hand (mobile group). The load cells mechanically connect these two groups. The support plate, if present, is then generally hidden by an external cover integral with the measurement plate. Visually, only the moving part is usually visible.

In a sandwich architecture, two groups are defined that move in relation to each other: the base frame 108 (and associated elements) on the one hand (fixed group), and everything else on the other (mobile group). The load cells mechanically connect these two groups. Visually, the two groups are generally visible.

Figure 3:
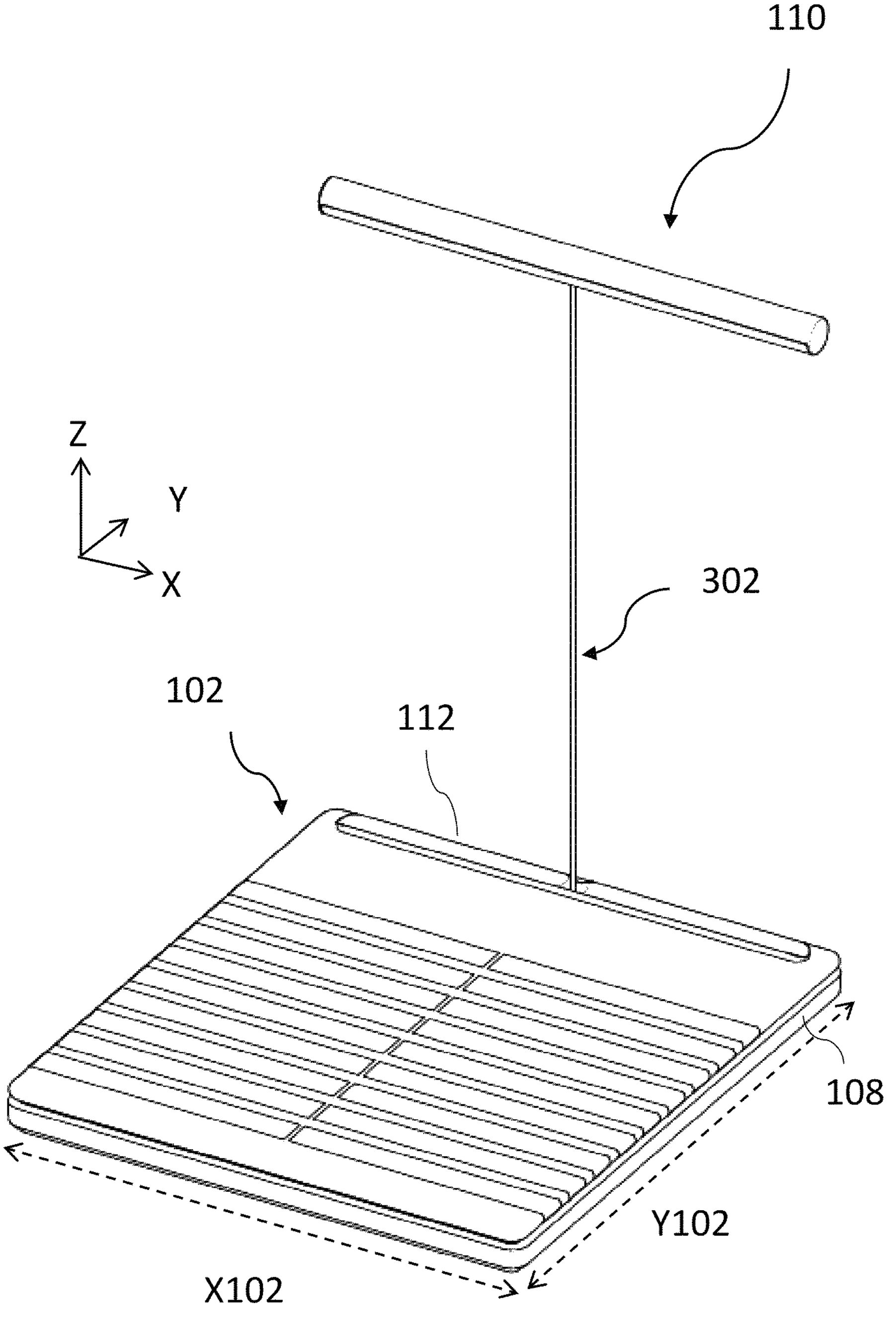
FIG. 3 represents a three-dimensional view of the station of FIG. 1; but with the handle in the extended position.
Figure 4:
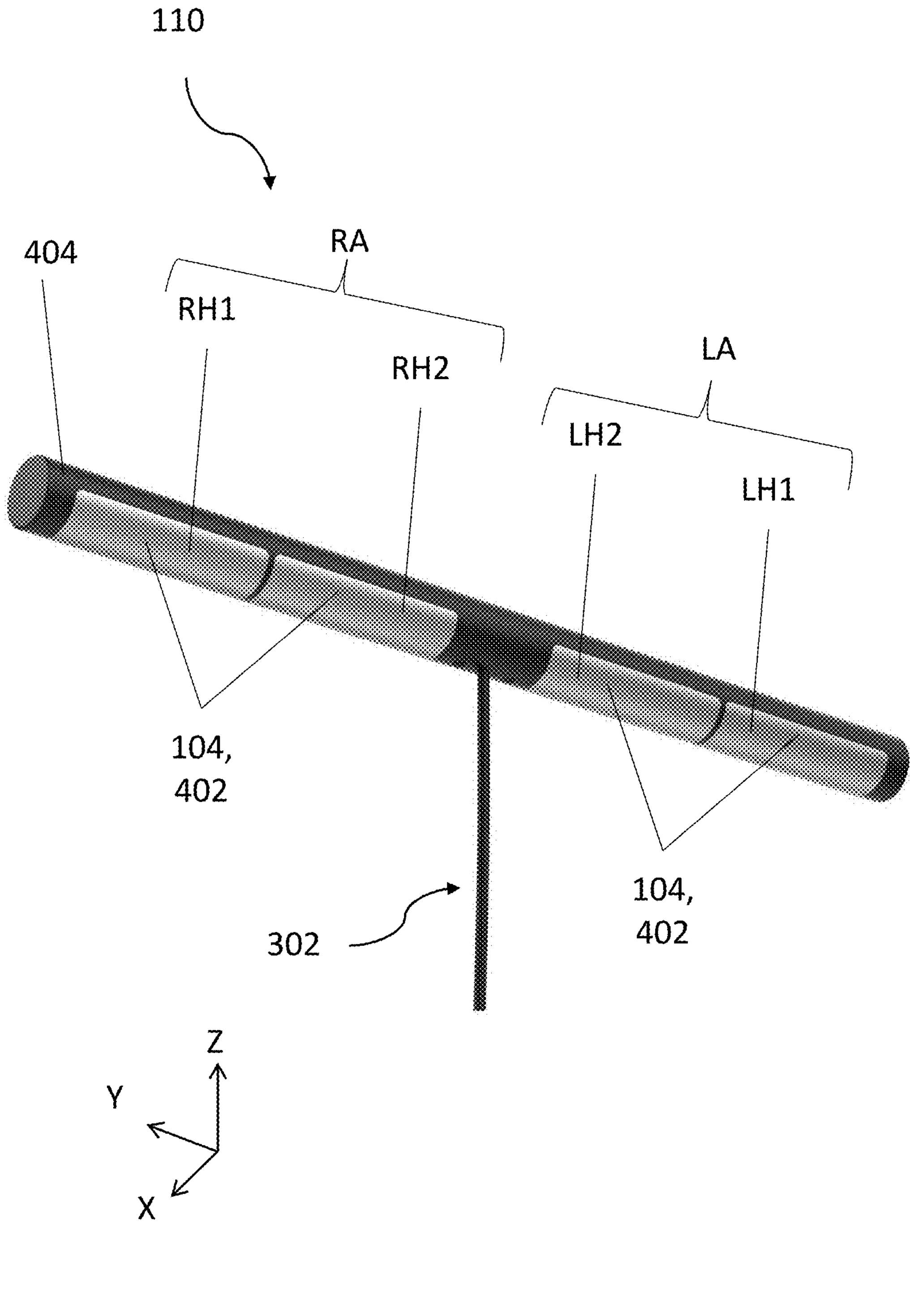
FIG. 4 shows a detailed view of the handle.

In an embodiment, the measurement station 100 further comprises a handle 110, suitable for gripping by at least one hand of the user, shown in FIGS. 3 and 4. The handle 110 may be connected to the measurement station by a cable 302 (visible in FIG. 3). In particular, the cable 302 allows electrical signals to be passed between the handle 110 and the base 102. In order to have a convenient measurement station 100 without a flying cable, the cable 302 may extend and retract (e.g., wind and unwind) within the base 102. The cable 302 may present a width comprised between 2 mm and 5 mm, notably 3 mm. In the extended position, the cable 302 may extend on a length greater than 1 m long. The cable 302 comprises an electric wire to transmit the electrical signals from the handle 110 to the base 102. The cable 302 comprises a braided sleeving arranged around the wire to protect it from the outside. The sleeve may be in textile, in polyethylene or in nylon. The cable 302 is flexible to enable an easy wind and unwind. In the extended position, the cable 302 is mechanically recalled towards the retracted position. The cable 302 is configured to be maintained easily in the extended position by a user standing on the measurement station 100 and holding the handle 110 in his or her hands. To this end, a reel (visible in FIG. 8 as element “802”) is arranged in a space provided between the substrate 106 and the base frame 108. At least two positions are thus defined for the handle: a stowed position (visible in FIGS. 1 and 2) and an extended position (visible in FIG. 3). Thus, the handle is movable at least between the stowed position and the extended position. The base 102 further includes a handle support 112 that may accommodate the handle 110 in the stowed position. The handle support 112 is, for example, mounted to the substrate 106. The handle support 112 may be an attachment to the measurement plate 106. For example, the handle support 112 may be glued to the measurement plate 106 (particularly when the measurement plate 106 is made of glass) or it may be screwed on. It will be described in more detail later. The handle 110 also includes at least one sensor 402.

The handle 110 is used to perform at least one of the following measurements: ECG (ECG-1-channel between the two hands or multiple channels with other limbs), BIA (so-called “segmental”), IPG. The sensors of the handle 110 are selected in particular from: optical sensor for PPG and electrodes.

The base 102 may include a display 114 (e.g., a screen or an LED or e-ink display) for displaying information to the user. The display 114 is shown dotted in FIG. 1 because, in the example figures, it is not or only minimally visible when turned off.

The base frame 108 of the base 102 may include a chamfer 204 to facilitate gripping the measurement station 100 while on the ground.

In an embodiment, the base 102 has a substantially rectangular shape in an XY plane. For example, the base 102 has a substantially parallelepiped shape in XYZ space.

When the measurement station 100 is positioned flat, the measurement plate 106 is parallel to a plane XY. The measurement station 100 comprises a longitudinal direction in a plane XY and a transverse dimension in a plane XY and orthogonal to the longitudinal direction. By height is meant the dimension along the Z axis (also called thickness); by width is meant the dimension transverse along the X axis; by length is meant the dimension longitudinal along the Y axis. In normal use, the user’s feet are positioned along the length Y of the base 102. The edge of the measurement station 100 (or base 102, or measurement plate 106) that is closest to the front part of the foot in normal use (i.e., the toes) is referred to as the front edge 206 and the opposite edge of the measurement station 100 (or base 102, or measurement plate 106), which is closest to the rear part of the foot in normal use (i.e., the heel) is referred to as the rear edge 208. A median axis may be defined, along the length Y (longitudinal thus), about which the measurement plate 106 is symmetrical and which allows to define a left part, intended for the left foot, and a right part, intended for the right foot. The width X102 of the base 102 may be between 330 and 400 mm, limits included (for example, about 357 mm) and the length of the base Y102 may be between 300 and 360 mm, limits included (for example, about 325 mm). The term “about” as used herein covers value deviations of +/−5%. The length and/or width of the measurement plate 106 may be slightly less than the length and/or width of the base frame 108, such that the measurement plate 106 is slightly recessed from the base frame 108. In this case, the length and width of the base frame 108 correspond to the length and width given above for the base 102, respectively. Such a design protects the measurement plate 106 from impact and contact with the external environment. Application FR2106653, incorporated by reference, describes such a solution. The term “slightly” as used herein covers a value difference of less than 10%, for example less than 5%.

Specifically, as illustrated in FIG. 2: the height Z102 of the base 102 may be between 20 and 35 mm, limits included (e.g., between 35 and 40 mm, limits included), and the maximum height Z100 of the measurement station 100 may be between 45 and 55 mm, limits included (e.g., 51 mm). As illustrated in the figures, only the handle support 112 and the handle 110 protrude along the Z direction from the measurement plate 106. Detailing the various dimensions: the height Z108 of the base 108 may be between 10 and 20 mm, limits included (e.g. 18 mm), the height Z202 of the support plate 202 may be between 3 and 6 mm, limits included (e.g.

4 mm), the height Z106 of the measurement plate 106 may be between 4 and 8 mm, limits included (e.g. 6 mm).

The cable 302 may be between 50 cm and 120 cm long, limits included. The length is chosen so that most users may grip the handle while standing with their hands down (at rest).

The measurement station 100 may, however, have different shapes and/or dimensions, provided that the shape and/or dimensions allow for the measurements herein described to be obtained. In particular, the base 102 may have an oval or more rounded shape in the XY plane.

The measurement station 100 may have a mass of between 3 and 6 kg, limits included (for example between 4 and 5 kg, limits included).

Using the sensor(s) on the base 102 and/or the sensor(s) on the handle 110, the measurement station 100 may perform a set of measurements on the user. In particular, the sensors 104 used include electrodes that are formed from electrically conductive paths mounted on the substrate 106 and/or the handle 110 (metal inserts, metal deposits, etc.). Some measurements may require only sensors on the base 102, other measurements may require only sensors on the handle 110, other measurements may require sensors on the handle 110 and the base 102 simultaneously.

The measurement station 100 may thus perform an ECG using the handle 110 (e.g., a 1-channel ECG), or an ECG using the handle 110 and the base 102 (e.g., a multi-channel ECG, such as a six-channel ECG). The measurement station 100 may thus perform a body impedance analysis BIA using the handle 110 and/or the base (between legs BIA and/or segmental BIA). The measurement station may thus perform an IPG in the leg arch ("between legs") or IPG in the foot ("in the foot").

The sensors may comprise electrodes adapted to: measure and/or apply a voltage (DC or AC) and/or a potential (DC or AC), and/or inject and/or recover a current (DC or AC). The functions of these electrodes may be selected from the following list: i+ and i−, for injecting AC current into the body of a user; V+ and V−, for measuring a potential difference in the body of a user; RA, LA and LL, for measuring an electric current flowing through the body of a user. Electrodes i+ and i−, V+ and V− are used for a BIA, IPG or ICG; electrodes RA, LL, LL are used for an ECG.

In particular, the measurement station 100 is configured to perform different measurements. Since the number of electrodes is limited (due to area and number considerations), the measurement station 100 has a particular arrangement of electrodes, with a switch.

As noted above, the sensors may include load cells, whereby the measurement station 100 may measure a weight and perform a BCG.

The handle 110 is illustrated in detail in FIG. 4. The handle 110 allows the measurement station 100 to perform a greater variety of measurements or alternatively more comprehensive measurements, through an electrical connection with at least one or even the two hands. In particular, segmental BIA and/or multi-channel ECG are made possible by the addition of the handle 110 to the base 102. The sensors 402 of the handle 110 include, for example, electrodes adapted to measure and/or apply a voltage and/or potential and/or inject and/or recover a current.

In an embodiment, in the stowed position, the handle 110 is in proximity to the leading edge 206. That is, the handle support 112 is in close proximity to the leading edge 206. For example, the handle support is at most between 1 cm and 3 cm, limits included, from the front edge 206.

In an embodiment, the handle 110 includes four electrodes, arranged in two pairs: a pair for the left hand and a pair for the right hand. For this purpose, the electrodes of the handle are referred to as: electrodes LH1, LH2, side by side on a left part of the handle 110 and electrodes RH1, RH2, side by side on a right part of the handle (by left, respectively right part is meant the part of the handle intended to be in contact with the left, respectively right hand). "Side by side" here means with a space between the electrodes, to insulate the electrodes from each other. Thus, the electrodes are arranged in succession between two ends of the handle 110. When the handle 110 is straight, the electrodes are arranged in sequence along the main direction of the handle 110. The electrodes LH1 and RH1 are positioned axially on the side of one end of the handle; the electrodes LH2, RH2 are positioned axially on the side of the center of the handle. Thus, in order, we have the following electrodes: LH1, LH2, RH2, RH1.

In an embodiment, the sensors 402 of the handle 110, when they are electrodes, are formed as a plurality of metal inserts in the handle 110. Materials that may be used for the metal inserts include stainless steel, titanium, brass, ITO or conductive plastics. For signal processing and/or acquisition, in particular ECG, the handle 110 may include processing electronics (operational amplifier tracker, etc.), in particular for ECG. It is generally desirable to amplify the signal as close to the electrodes as possible because the cable may pick up ambient noise.

Figure 5:
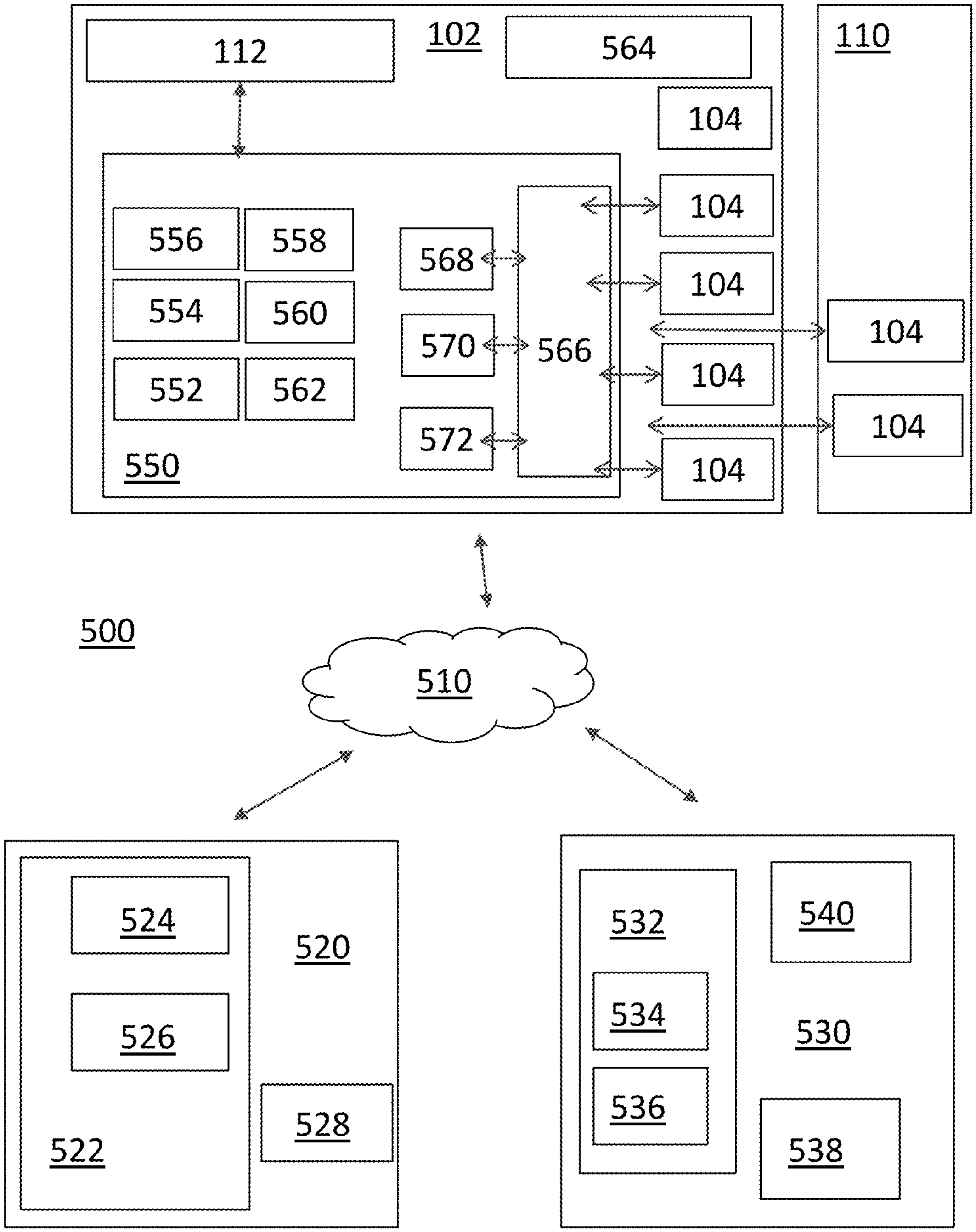
FIG. 5 shows a schematic view of the measurement station and its surroundings.

FIG. 5 illustrates a schematic view of the overall architecture 500 into which the measurement station 100 may be inserted. This overall architecture forms a system comprising the measurement station 100. In particular, the measurement station 100 may communicate with third party devices via a communication network 510, which is for example a wireless network (in particular a network compatible with at least one of the following communication protocols: BlueTooth, Wi-Fi, cellular, etc.). The third-party devices may include a server 520 and a mobile terminal 530 (smartphone, etc.). The server 520 may include control circuitry 522, including a processor 524 and a memory 526, and an input/output ("I/O") interface 528, which allows the control circuitry to receive and send data to the communication network 510. The memory 526 may store code instructions, which, when they are executed by the processor 524, perform various functions of the server 520. The mobile terminal 530 may include control circuitry 532, including a processor 534 and a memory 536, and include an input/output (I/O) interface 538, which allows the control circuitry to receive and send data. The memory 536 may store code instructions, which, when they are executed by the processor 534, perform various functions of the mobile terminal 530. The server 520 is a remote server, for example, located in a data center. The mobile terminal 530 further includes a user interface 540 ("UI") configured to display information to the user and allow the user to enter information (such as height, gender, etc.), if necessary. In particular, the control circuitry 532 is configured to run an application managing the environment of the measurement station 100. The mobile terminal 530 is a personal object of the user, typically in close proximity to the user.

The measurement station 100 may communicate with the server 520 and/or the mobile terminal 530. In an embodiment, the measurement station 100 may communicate directly with the mobile terminal 530, for example via Bluetooth or Bluetooth Low Emission (BLE). This communication may be implemented at the installation of the measurement device 100, in particular to pair it with the mobile terminal 530 and/or to configure a connection to the server 520 that does not transit through the mobile terminal 530 and/or as a backup for a failed communication with the server 520. In an embodiment, the measurement station 100 may communicate directly with the server 520, without transiting through the mobile terminal 530. This communication allows the user to use the measurement station even without having his mobile terminal 530 nearby.

The measurement station 100 also includes control circuitry 550 with a processor 552 and a memory 554, and an input/output (I/O) interface 556, which allows the control circuitry to, among other things, receive and send data to the communication network 510. The processor 552 is configured to, among other things, process data obtained by the sensors 104. In particular, the processor 552 may execute instructions from a program stored in the memory 554. The control circuitry 550 may include a microcontroller, which integrates the processor 552, the memory 554 and the input/output interface 556. The control circuitry 550 may further include an analog front end ("AFE") device. The control circuitry 550 may also include an analog to digital converter ("ADC"). The measurement station 100 includes a voltage source 558 (e.g., DC) and a current source 560 (e.g., AC). The measurement station 100 also includes a voltmeter 562 (or any system for measuring a voltage). The voltmeter 562 may be integrated with the AFE. The current source 560 may be integrated with the AFE and the voltage source 558 may be integrated with the microcontroller MCU (e.g., via a digital-to-analog converter DAC). Some of the sensors 104 (in particular the sensors 402 of the handle 110 in FIG. 4 or the electrodes 602 of the handle 110 in FIG. 6A) are connected to the control circuitry 550 (e.g., to the MCU or to the AFE). The measurement station 100 includes a battery 564, suitable for supplying power to the various components of the measurement station 100.

The control circuitry 550 and other electronic components may be mounted on a printed circuit board ("PCB"), which is attached to the support plate 202, for example. Connectors connect the electrical conductive paths from the measurement plate to the PCB. In order to change the connections of the electrodes to the various components of the measurement station 100, the measurement station includes a switch 566. The switch 566, which may include a plurality of switches controlled by the microcontroller MCU, will be described in more detail later.

The control circuitry 550 includes, for example, an ECG acquisition system, an impedance measurement system (for BIA or IPG), an ESC system (for ESC). The ECG acquisition system comprises electrodes (represented by 602 in FIGS. 6*a* and 6*b* and 402 in FIG. 4) and an ECG electrical circuit 568 (which incorporates, inter alia, various amplification and/or filtering stages and a demodulator); the impedance measurement system comprises, in particular, electrodes (represented by 602 in FIGS. 6*a* and 6*b* and 402 in FIG. 4), the current source 560, the voltmeter 562 and an impedance measurement electrical circuit 570 which connects the electrodes to the current source and to the voltmeter (which incorporates various amplification and/or filtering stages): the ESC system includes electrodes, the voltage source 558, and an ESC electrical circuit 572 (which incorporates various electronic components, including resistors). The switch 566 is used to connect the sensors 104, e.g., electrodes, to, among other things, the various circuits 568, 570, 572 mentioned above, or to disconnect all sensors and/or electrodes from the control circuitry 550.

The control circuitry 550 is essentially located in the base 102, except for a few components (amplification, filtering and switches) located in a PCB in the handle 110, to process the signals before they are passed through the cable 302.

As previously mentioned, the measurement station 100 also includes the display 114, such as a screen (OLED/PMOLD, Retina, etc.), for displaying information to the user. Alternatively, the measurement station 100 does not include a display.

Figure 6B:
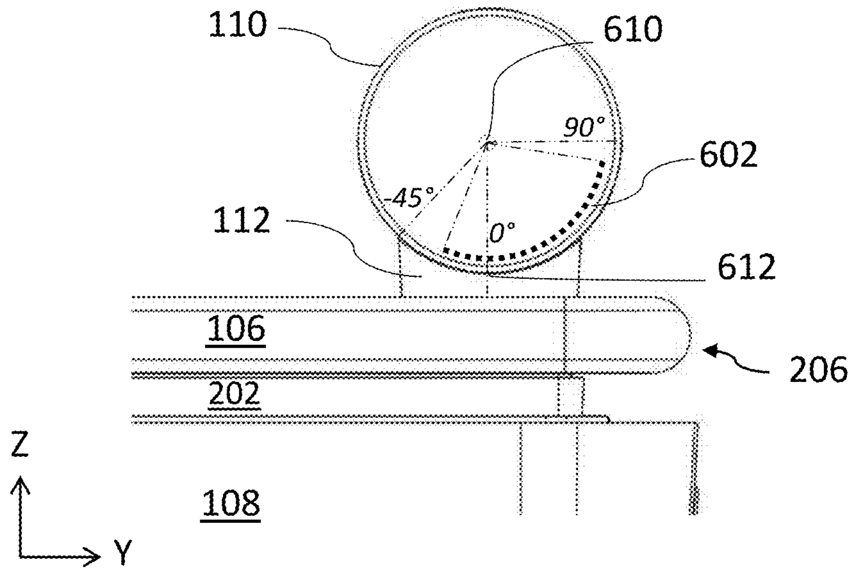
FIG. 6B illustrates a side view of the handle on a handle support of the base, according to an embodiment of the invention.
Figure 6A:
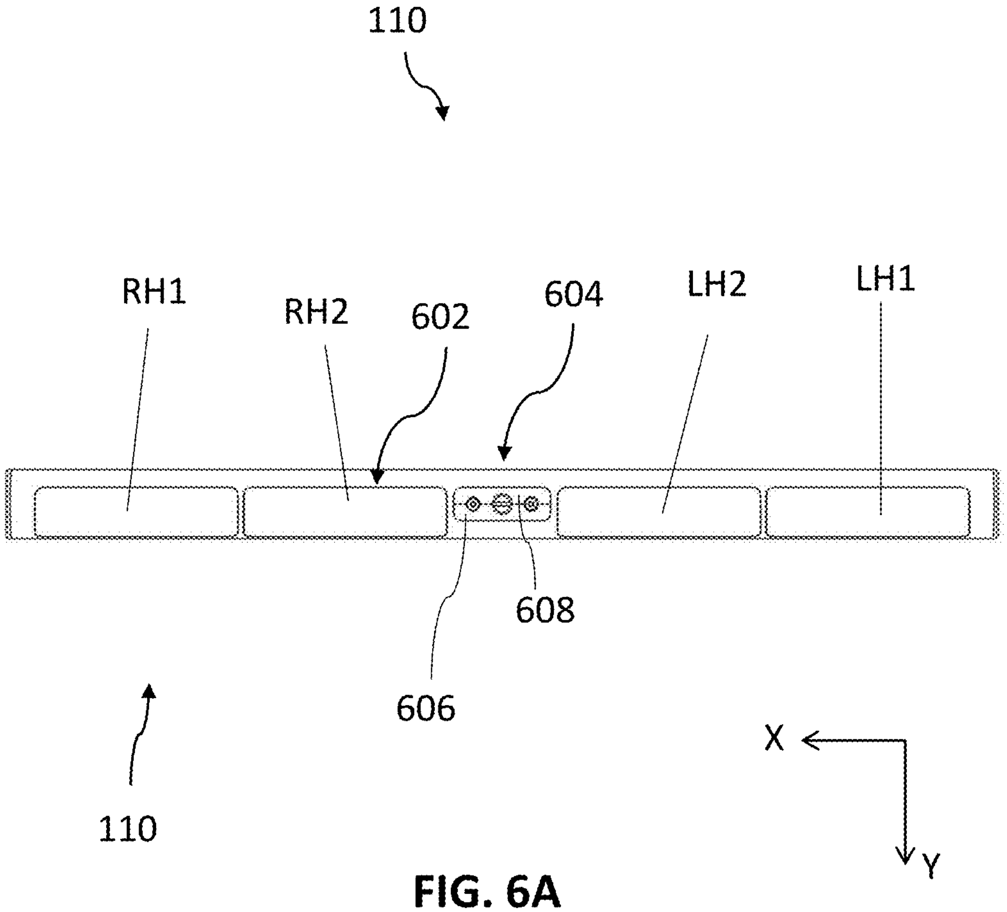
FIG. 6A illustrates a detailed view of the handle, according to an embodiment.
Figure 7:
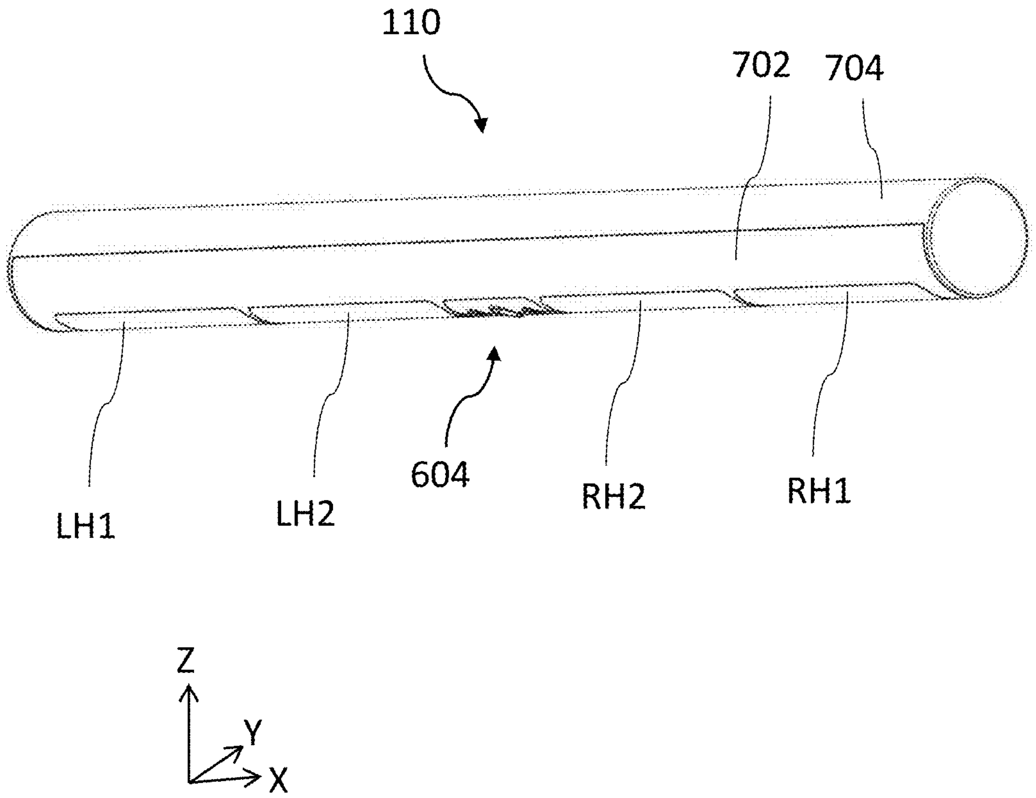
FIG. 7 illustrates a three-dimensional view of the handle, according to an embodiment.

The handle 110 is illustrated in detail in FIGS. 4, 6 and 7. The handle 110 allows the measurement station 100 to perform a wider variety of measurements or alternatively more comprehensive measurements through electrical connection with at least one hand, for example both hands. In particular, segmental BIA and/or multi-channel ECG are made possible by the addition of the handle 110 to the base 102. The sensors 402 of the handle 110 include, for example, electrodes 602 adapted to measure and/or apply a voltage and/or potential and/or inject and/or recover a current.

As previously described, in an embodiment, the handle 110 includes four electrodes, arranged in two pairs: a pair for the left hand and a pair for the right hand. For this purpose, the electrodes of the handle are referred to as: electrodes LH1, LH2, side-by-side on a left portion of the handle 110 and electrodes RH1, RH2, side-by-side on a right portion of the handle (by left, respectively right portion, is meant the portion of the handle intended to be in contact with the left, respectively right hand; and by side-by-side is included a spacing between the electrodes). The electrodes LH1 and RH1 are positioned axially on the side of one end of the handle; the electrodes LH2, RH2 are positioned axially on the side of the centre. Thus, in order, there are the following electrodes: LH1, LH2, RH2, RH1. Cable 302 enters the handle between electrodes LH1, LH2 on one side and electrodes RH1, RH2 on the other.

As illustrated in FIG. 6B, the electrodes 602 are positioned offset from where the cable 302 enters the handle 110. In the case of a cylindrically shaped handle of axis A, parallel to the transverse direction X of the measurement station 100 in the stowed position, where the position of insertion of the cable 203 into the handle 110 defines 0°, the electrodes extend over an external surface of the handle 110 between −45° and +90°, limits included, (in the trigonometric direction with respect to the orthonormal reference frame XYZ), or even between −30° and 80°, limits included. In the embodiment of the figures, the electrodes extend from −30° to +79°, limits included, (angle covered by the electrodes of 109°, plus or minus 1°). The angles are defined in a cross-section of the handle 110 (a cross-sectional plane orthogonal to the axis A thus a YZ cross-sectional plane when the handle 110 is positioned in the handle support 112). Positive angles between 0 and +180°, limits included, are oriented toward the edge closest to the base 102. In other words, in the stowed position, the electrodes extend on the handle more on the side of the front edge 206 of the base 102 than on the side of the rear edge 208.

More generally, for any shape of the handle (straight, slightly curved, non-cylindrical, etc.), the positioning of the electrodes may be defined as follows. The handle 110 includes a midline 610, which is a line passing through the center of the volume defined by the handle 110, i.e., a line defined by the isobarycenters of successive cross-sections of the handle 110 (isobarycenter of the curve defined by the outer surface of the handle 110 in a cross-section). The handle 110 includes a bottom line 612, which is a line defined, for successive cross-sections of the handle 110, by the set of points on the outer surface of the handle 110 that are closest to the measurement plate 106 (in a stowed position). For each section transverse to the centerline, the angle through the centerline and an end of the electrodes 602 on an outer surface of the handle 110 is defined. The angle 0° is defined as that between the midline and the bottom line; positive angles are defined from 0° going to the side of the leading edge 206 and negative angles are defined from 0° going toward the trailing edge 208 (thus the angles range from −180° to +180°). The cable 302 enters the handle 110 at the 0° angle (i.e., the entry point of the cable 302 into the handle 110 is at 0°. For each section transverse to the centerline 610 that includes an electrode portion 602, the electrode 602 extends at most over an area of the handle between −45° and +90°, limits included, particularly between −30° and 80°, limits included. In an embodiment, the electrodes extend from −30° to +79° (total angle covered by the electrodes of 109°, plus or minus 1°).

This positioning of the electrodes has several benefits. When gripping the handle 110, the cable 302 generally remains downward, aligned with the vertical Z. Consequently, firstly, with a natural and intuitive grip, the positioning of the electrodes allows an optimized contact with the fingers, by allowing a contact of the electrodes with all the fingers: the intermediate phalanges of the longest fingers, the intermediate phalanges or the distal phalanges of the shortest fingers. Secondly, by avoiding contact with the phalanges of the fingers, the handle 110 may be used with rings. Third, the electrodes are positioned downwards, i.e. they are oriented towards the ground: the weight of the handle, of the cable and possibly a ratio force of the cable participate in maintaining the electrodes in contact with the fingers which are wrapped under the handle 110 and thus on the electrodes. Fourth, the position of the four electrodes along the direction A allows the electrodes to all be in contact with a hand in a natural and intuitive grip of the handle 110.

The handle 110 may include a main body 404 on which the electrodes and other components (electronics, fastener, etc.) are mounted. The main body 404 may have an elongated shape along a longitudinal axis (which is parallel along the X direction in the stowed position), for example generally cylindrical and more specifically rotationally cylindrical. The shape is selected to be grippable by a user. To facilitate assembly, the main body 404 may include a first portion 702 and a second portion 704. The first portion 702 may receive the electrodes 402 and the second portion 704 may be mounted to the first portion 702. In particular, the second portion 704 may comprise a cylindrical (e.g., rotationally symmetrical) cross-section with two ends (e.g., flat or rounded). An area of the sidewall of the cylindrical section may be absent (e.g., from one end to the other) in order to accommodate the first portion 702 of the main body 404. A plastic material may be used for the main body, in order to keep the handle light (in case of a fall) and to insulate the electrodes 402 well from each other.

In an embodiment, the electrodes 402 are formed as a plurality of metal inserts in the main body 404. Materials that may be used for the metal inserts include stainless steel, titanium, brass, ITO (indium tin oxide), nickel (or nickel alloy) or conductive plastics. For signal processing and/or acquisition, in particular ECG, the handle 110 may include processing electronics (amplification, filtering, etc.), particularly for ECG. It is generally desirable to amplify the signal as close to the electrodes as possible because the cable may pick up ambient noise.

In the stowed position, the first portion 702 faces the base 102 and the second portion 704 is visible. The electrodes 402 are thus disposed against the handle support 112.

In an embodiment, the handle 110 is removable, particularly for repair purposes. To this end, the handle 110 includes a fastening system 604 for connecting the handle 110 to the cable 302. The attachment system 604 allows the handle 110 to be simply changed without changing the cable 302. The attachment system 604 may be mounted in the first portion 702 of the handle. This positions the electrodes on the side of the cable 302, which provides a natural contact position between the electrodes 402 and the user's fingers. The fastening system 604 may include a jaw 606, 608 that arranges around a stopper mounted on the cable 302.

In an embodiment, the handle support 112 and the handle 110 comprise a magnetic attachment system (e.g., by means of at least one permanent magnet). A magnetic material is provided in the handle support 112 and a magnet is mounted in the handle 110 (or vice versa). The magnet attachment systems also serve as a deception device when positioning the handle 110 on the handle support 112 (i.e., the left side of the handle cannot be placed on the right side of the handle support due to the polarities). Neodymium magnets may be used.

As previously mentioned, the cable 302 may be stored in the base 102 (in the stowed position, visible in FIGS. 1 and 2) and out of the base 102 (in the extended position, visible in FIG. 3).

In order for the cable 302 to more naturally move into a stowed position, the end of the cable 302 attached to the handle 110 extends orthogonally with respect to a surface of the handle. In particular, the handle shown in the figures has a cylindrical shape: the cable 302 therefore extends radially with respect to the cylinder.

Figure 8:
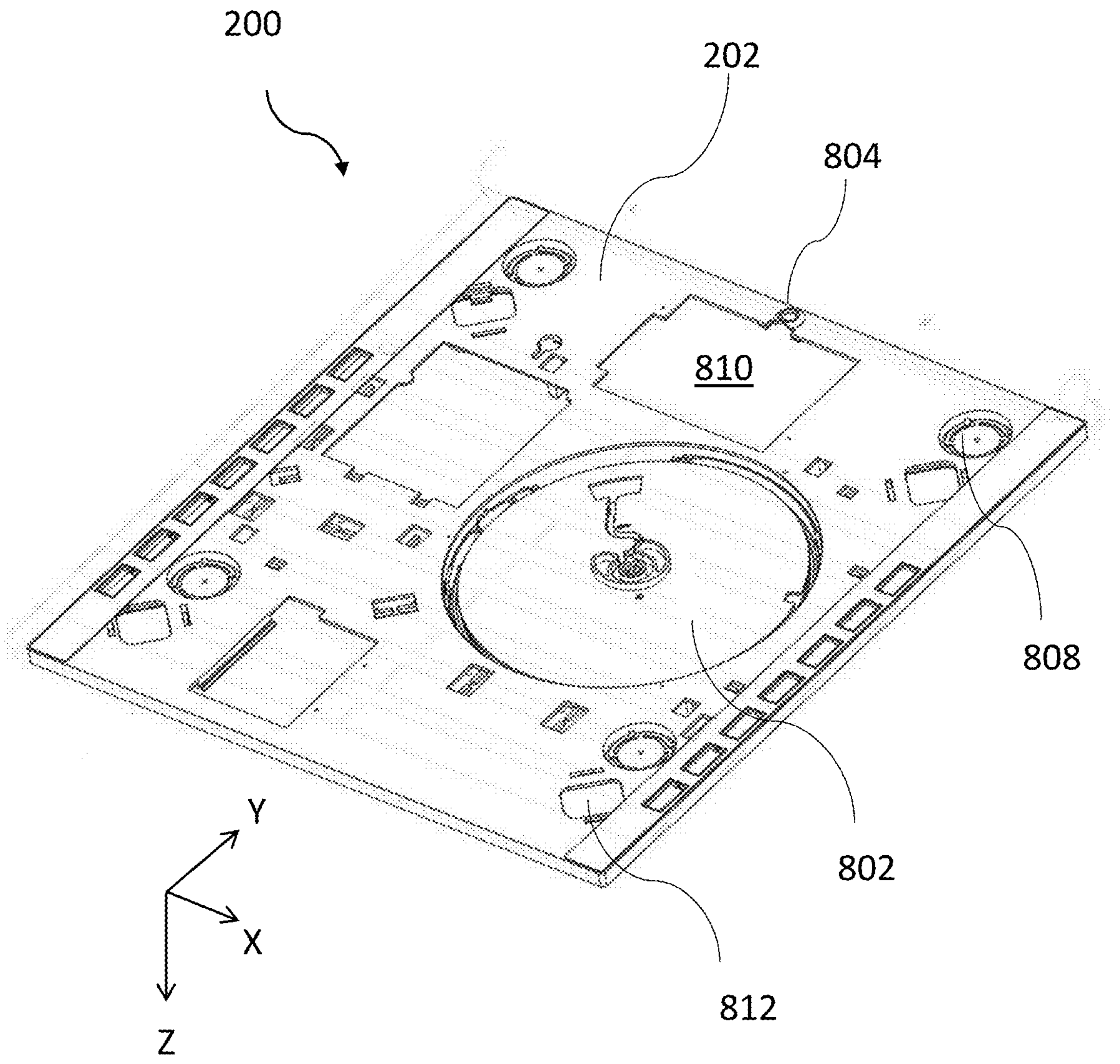
FIG. 8 illustrates a three-dimensional view, in transparency, of a support plate, according to an embodiment.

The change in position between a stowed position and an extended position therefore involves a displacement of the cable 302 relative to the base. It is desirable, for reasons of safety and practicality, that the cable 302 is almost completely housed in the base 102 in the stowed position. In order to make this possible without any particular effort by the user, a return mechanism 802 is mounted in the scale. In an embodiment, this return mechanism is a reel, i.e., the cable 302 reels in and out when the user prepares to use the handle 110. FIG. 8 illustrates the positioning of such a reel 802 (shown without its cover) in the base 102. The reel 802 is, for example, mounted to the support plate 202, which may include a through opening 902 to accommodate the reel (to minimize the thickness of the base 102). The reel 802 may include mounting tabs that are screwed to the support plate 202. The reel 802 includes, for example, a fixed portion and a movable portion, with a spring therebetween to provide a return function when the handle 110 is in an extended position or in an intermediate position. WO2021/082876 describes an example of a reel mechanism incorporated into a bathroom scale.

To guide the cable 302 between the reel 802 and the handle 110, different solutions are proposed, which may be implemented together or separately.

The measurement plate 106 includes a plate through-hole 1102 for the passage of the cable 302. The radial orientation of the cable 302 relative to the cylinder of the handle allows the cable to be inserted directly into the through hole 1102 of the measurement plate 106. The through-hole 1102 is, for example, cylindrical (i.e., straight through). The through-hole 1102 may be orthogonal to the measurement plate 106 (parallel to the Z-axis, thus, not at an angle), to facilitate pulling the handle 110, for example, a straight cylindrical shape. The through-hole 1102 may have a cross-sectional area equivalent to that of the cable 302 (with a slight functional clearance). For example, the through hole 1102 is cylindrical in shape. For example, the maximum cross-sectional dimension of the hole is 2 cm or 1 cm.

In particular, the support plate 202 and the measurement plate 106 each include a through hole 804 and 1102, opposite each other, for the passage of the cable 302.

Figure 10:
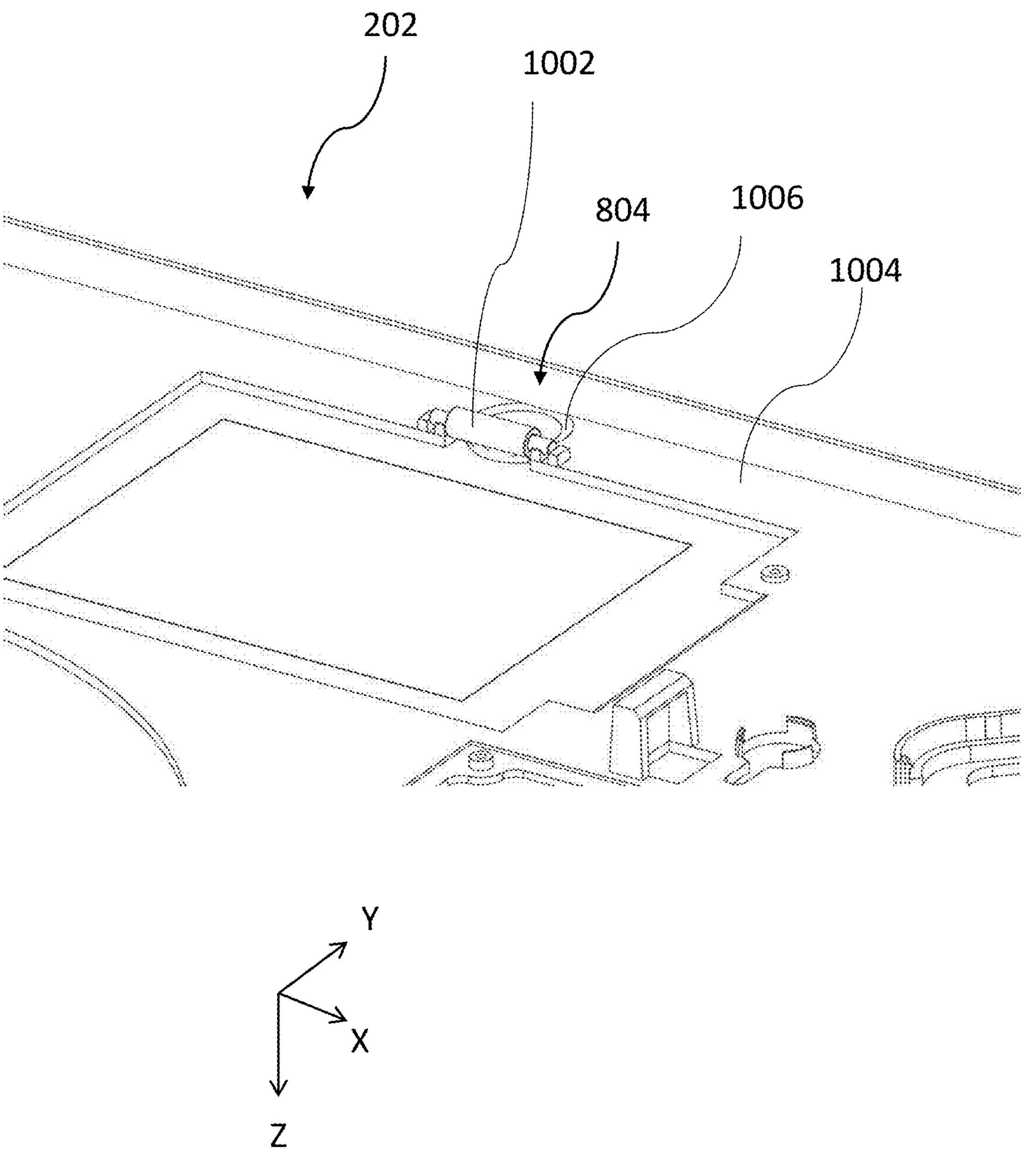
FIG. 10 illustrates an enlargement of a portion of a support plate, according to an embodiment.

The reel 802 winds and unwinds the cable 302 in the XY plane (essentially along Y) while the handle 110 (and thus the portion of the cable outside the base 102) moves along the Z direction. Therefore, the cable 302 makes one or more changes in direction. In the vicinity of the hole 804 of the support plate 202, a roller 1002 (or pulley) is arranged to facilitate the change of direction of the cable 302 (and avoid friction that both deteriorates the cable 302, the support plate 202 and/or the handle support 112 and hinders the winding and unwinding of the cable. The roller 1002 may be a rotating roller or simply a roller with a smooth coating. As shown in FIG. 10 (which illustrates a portion of the support plate 202), the roller 1002 may be mounted on the support plate 202 (on the bottom side 1004, i.e., the side that is toward the ground when the measurement station 100 is in the position of use). The roller 1002 is arranged to be, along the Z-direction, between the cable 302 and the support plate 202 (or the measurement plate 106). A second roller (not shown) may be provided between the roller 1002 and the reel 802 to channel the cable. The second roller may be arranged such that the cable 302 is between the second roller and the measurement plate. Alternatively, the second roller is opposite the first roller 1002. The two rollers are thus on opposite sides of the cable 302 (along the Z direction). Instead of the roller, a pulley or any element performing a similar function may be used.

To limit friction when passing through the through hole 804 of the support plate 202 and to smooth the angle made by the cable 302, the edges of the hole are chamfered (chamfer 1006 visible in FIG. 10), at least on the side of the lower face 1004. Similarly, to limit friction when passing through the hole 1102 of the measurement plate 106, the edges of the hole 1102 are chamfered (see FIG. 11: chamfer 1106 visible on the upper surface 1104 of the measurement plate 106, i.e., the visible face, on which the user places his feet). Since the measurement plate 106 may be made of glass and therefore sharp, the plate through hole 1102 is chamfered on both sides (see FIG. 12, which shows a perspective magnification: chamfer 1202 visible on the lower surface 1204 of the measurement plate 106, i.e., the invisible side, which faces the support plate 202).

In the example shown in the figures, the handle support 112 is a part that is placed, for example by gluing, on the upper surface 1104 of the measurement plate. Here, the handle support 112 has an elongated shape. The handle support 112 may form a cradle 1302, such as a rounded cradle. The cradle may have a shape complementary to a portion of the handle 110 (herein the first portion 702 of the handle 110. In the example shown in FIG. 6B, the cradle 1302 is rounded about a directional axis X. The handle 110, when positioned on the handle support 112 does not touch the measurement plate 106.

In particular, to ensure that the cable 302 is completely invisible in the stowed position, the handle support 112 includes a support through-hole 1304, which faces the hole 1102 of the measurement plate 106. The radial orientation of the cable 302 relative to the handle cylinder allows the cable to be inserted directly into the through-hole 1304 of the handle support 112. The through-hole 1304 is, for example, cylindrical (i.e., straight through). The through-hole 1304 may be orthogonal to the measurement plate 106 (parallel to the Z-axis, thus, not at an angle), to facilitate pulling the handle 110, for example, a straight cylindrical shape. The through-hole 1304 may have a cross-sectional area equivalent to that of the cable 302 (with a slight functional clearance). For example, the through hole 1304 is cylindrical in shape. For example, the maximum cross-sectional dimension of the hole is 2 cm or 1 cm.

Beneficially, the through hole 1304 is positioned at the bottom of the cradle 1302. The bottom of the cradle is defined as the lowest position along the Z direction, i.e., the position closest to the measurement plate 106. In addition, the through hole 1304 may be centered in the cradle along the Y axis. The movement of the cable 302 may, from the through hole 1304 in the handle support 112, become somewhat more erratic due to a user's use of the handle 110. Also, to limit friction, the through hole 1304 of the handle support 112 is chamfered. In particular, the edges of the through hole 1304 are chamfered in the Y direction and, may be chamfered along the X direction (same chamfered all around). Thus, a chamfer 1306 is provided on at least one of the two opposite edges along Y of the through hole 1304. Similarly, a chamfer 1306 may thus be provided on at least one of the two opposing edges along Y of the through-hole 1304.

The cradle 1302 may extend over an angle at least equal to the negative value of the position of the electrodes 602 on the handle 110 relative to the bottom of the cradle (which corresponds to the angular position of the through hole 1304 and thus the location of the cable 302 in the figures, i.e., −30° in the illustrated example. In other words, in the given example, in a cross-section (a YZ cross-sectional plane), the cradle extends 30° between its end and the bottom of the cradle (which here corresponds to t)e angular position of the through hole 1304. By having a cradle that extends over an angular portion (about an axis parallel to the X direction) at least equal to that of the electrodes, the latter are invisible when the measurement station 100 is observed from the rear edge 208, which corresponds to its most frequent positioning by the user since the front edge 206 is generally against a wall) because they are hidden by the cradle 1302 (see FIG. 6B). This concealment increases the retention of the measurement station 100 (i.e., the fact that most users of the measurement station 100 continue to use the measurement device after a given period of time) because the user does not have a sense of using a product with a medical or paramedical aspect.

Similarly, the cradle may extend over less than 90°, i.e. over an angle of at most 90°, or even at most 60°, or even 45°, on either side of a bottom of the cradle (which is defined as 0°—the through-hole also being at 0°), so as not to interfere with the grip of the handle. The fingers may then slide under the handle to remove it from the handle support 112. The value of 45° allows an easier grip while concealing the electrodes.

With the handle support 112, the design and manufacture of the measurement plate 106 is simplified. With the exception of the through hole 1102, the measurement plate 106 may be similar to that of a measurement station without a handle (hence simplifying processes to have several different designs, with and without handles, for example). Furthermore, by arranging the handle 110 on a handle support 112 arranged on the measurement plate 106, the handle 110 is easily gripped by a user, including by raising the stowed position relative to the measurement plate 106 along the Z direction. The cradle shape 1302 allows the handle 110 to be easily stored and thus not to be placed on the ground where it may get damaged, damage the base 102 or the ground on which it is placed. The arrangement of the cable 310 along the vertical direction 2, in alignment with the through holes 1304 and 1102 of the handle support 112 and the measurement plate 106 contributes to simplifying the stowed position of the measurement station 100 because it is sufficient to accompany the return force of the reel 802 for the handle 110 to be positioned in the cradle 1302 (in particular because of the positioning of the through hole 1304 at the bottom of the cradle 1302).

In the description above and in the figures, the handle support is continuous along the X direction. However, it may be discontinuous along this direction. For example, the cradle shape may be generated by two or three supports, at the ends and in the middle. This configuration is less concealing of the cable and the handle electrodes, however.

Alternatively, the measurement station 100 does not include a handle support, and the handle is placed directly on the measurement plate 106. The latter may be machined or molded to have a shape to receive and hold the handle 110 in place. For example, a cradle shape may be made in the glass. The through hole 1102 is then at the bottom of the cradle. The magnetic attachment system may then be provided in the handle and under the measurement plate.

In an embodiment, the measurement station 100 has a scale function, to measure a weight and thus a mass of a user. The sensors of the base 100 then comprise at least one weight sensor or mass sensor. In particular, a known solution is to use load cells, which convert a deformation of an element into an electrical signal. When the user climbs onto the measurement plate 106, his mass generates a force which is taken up by the measurement plate 106, then transmitted (directly by contact or indirectly via an intermediate part such as the support plate 202) to at least one load cell, and then the contact is taken up by the base 108 (or the feet for the footed architecture). Four load cells may be provided, proximate each corner of the base 102. When the base 102 is not rectangular, the load cells may be arranged regularly with respect to the geometry (for example, with symmetry about median axes).

Figure 9:
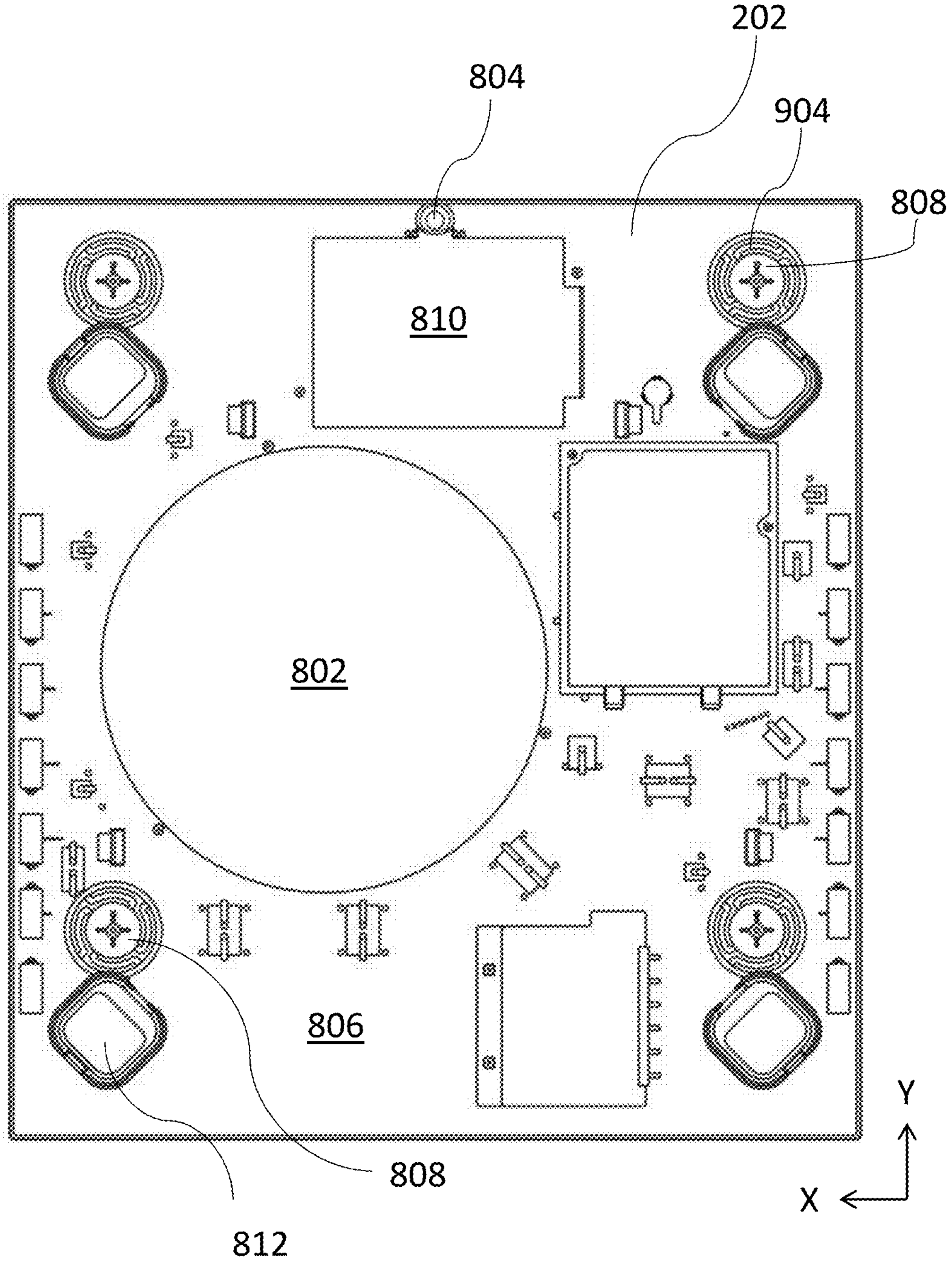
FIG. 9 illustrates a back view of a support plate, according to an embodiment.

In an embodiment illustrated in FIGS. 8 and 9, the support plate 202 includes holes 812 suitable for accommodating (without contact) the load cells. In this way, the support plate 202 does not interfere with the force transfer between the measurement plate 106 and the load cells.

However, in the sandwich architecture, the displacement in the XY plane of the mobile assembly (measurement plate 106, support plate 202 and other components, in particular electronic components) is limited with respect to the fixed assembly (the base 108 essentially). However, the limitation of this displacement should not contaminate the weight measurement, i.e., it should not interact with the displacement along the Z-direction or take up any force along the Z-direction. PCT/EP2017/050178 describes a satisfactory solution to this problem. The present description provides an alternative embodiment. The support plate 202 comprises at least one island 808, for example one island 808 per load cell (four in the figures, one in the vicinity of each load cell). The island 808 is a part of the support plate 202 that is connected to a main body 902 of the support plate base 202 by an elastic member 904. The resilient member 904 functions to limit the XY displacement of the movable assembly by minimally impeding the Z displacement. The resilient member 904 may include one or more legs extending between the island 808 and the main body 902 of the support plate 202. In the figures, each resilient member 904 includes four identical legs. Each island 808 is received in a through hole formed in the main body 902. The island 808 may have a circular, square, rectangular, or other shape (e.g., polygonal or of revolution) and the through hole may have a similar but homothetically larger shape.

Each island 808 includes an attachment hole 1402, for example in the form of a threaded hole, which is adapted to receive a rod, for example a screw, which attaches the base 108 to the island 808 (via an attachment hole 1502 in the base 108). The screw may be threaded. The attachment hole 1402 may be provided in a projection 1404, which makes it possible both to limit the length of the rod and to locally increase the thickness of the island 808 (more rigidity in the connection with the rod).

Figure 14:
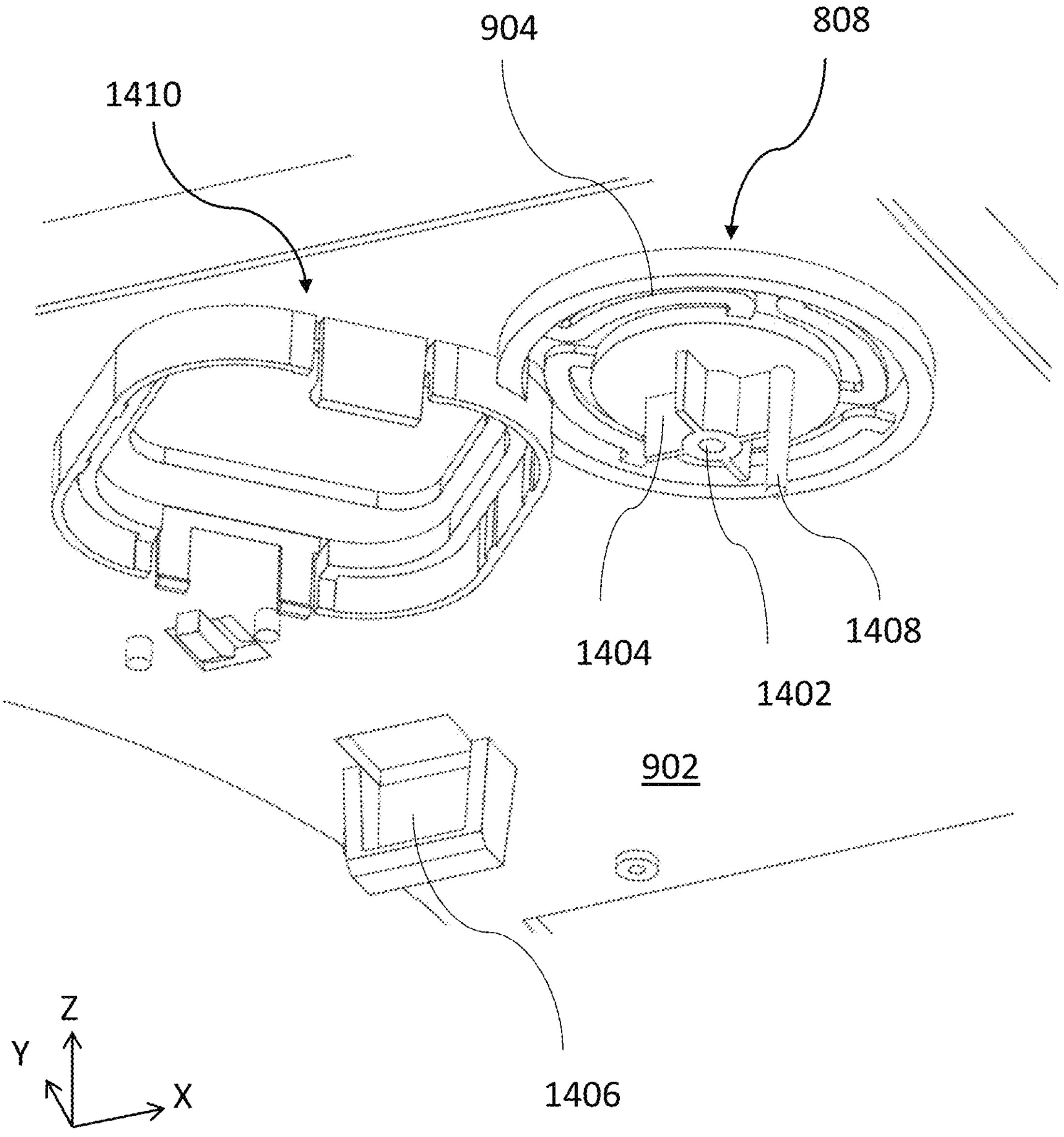
FIG. 14 illustrates a close-up view of a support plate, according to an embodiment.
Figure 15:
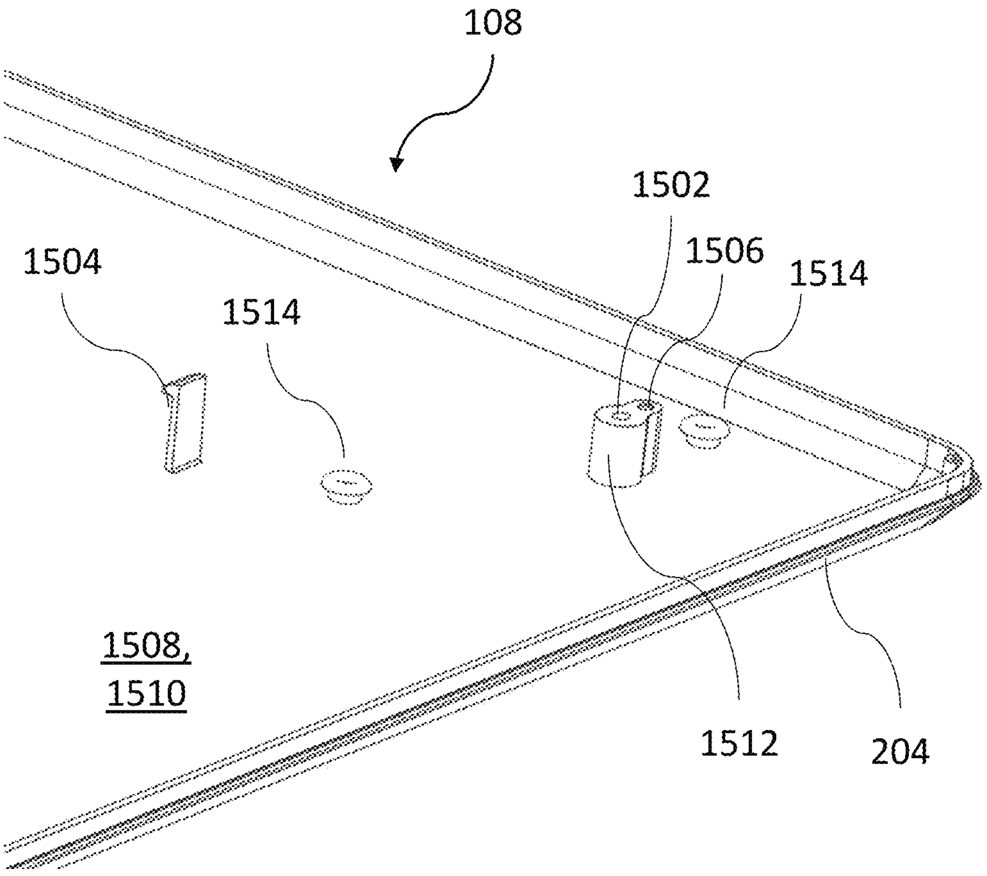
FIG. 15 illustrates a close-up of a bottom of the base, according to an embodiment.

Nevertheless, if a user grabs the measurement station 100 by the measurement plate 106 (which is part of the mobile assembly), the entire weight of the fixed part will pass through the rod and island 808. However, the elastic member(s) 904 are not strong enough to take up this force (recall that they are not intended to interfere with the weight measurement). The support plate 202 and the base 108 then include a maximum Z-displacement stop. As illustrated in FIGS. 14 and 15, the stop may take the form of an L-shaped tab 1504 of the base 108 (with a portion in Z is a portion in a plane parallel to the XY plane), which cooperates with a receptacle 1406 of the support plate 202 that includes a portion in a plane parallel to the XY plane so that a stop occurs when the Z displacement is too large. For example, the allowable Z-displacement is less than 1 mm.

The support plate 202 may be assembled to the base 108 by positioning the support plate 202 (or more generally the movable assembly) above the base. In this case, the attachment holes 1502 in the base and the attachment holes 1402 are all aligned in pairs in order to insert the rod (for example, to insert a screw). This alignment may take an operator a few seconds. To simplify the process, the measurement station 100 may include a guide between the moving assembly and the fixed assembly. The guide may take the form of a guide rod 1408 extending in a Z-shape and adapted to cooperate with a guide hole 1506 in the base 108. The guide rod 1408 may be located in close proximity (at a distance D) to the attachment hole 1402 of the corresponding island 808 (for example, less than 1 cm) so that the influence of manufacturing clearances is minimal. Similarly, the attachment hole 1502 of the base 108 is close to the guide hole 1506 (the same distance D). The guide rod 1408 comes to protrude in a Z direction from the level of the attachment hole 1402. In particular, even though the island 808 is configured to be integral in XY displacement with the main body 902, the resilient members 904 effectively impart XY resiliency; to counteract this undesirable displacement that may disrupt the assembly, the guide rod 1408 is mounted on said island 808. The guide rod 1406 is also used to block the rotation of the island 808 during screwing.

Conversely, the base 108 could have the guide pin and the island 808 could have the guide hole.

A hole 1410 is provided proximate to the island 808 to accommodate the load cell, so that it is positioned between the measurement plate 106 and the base 108.

Figure 16:
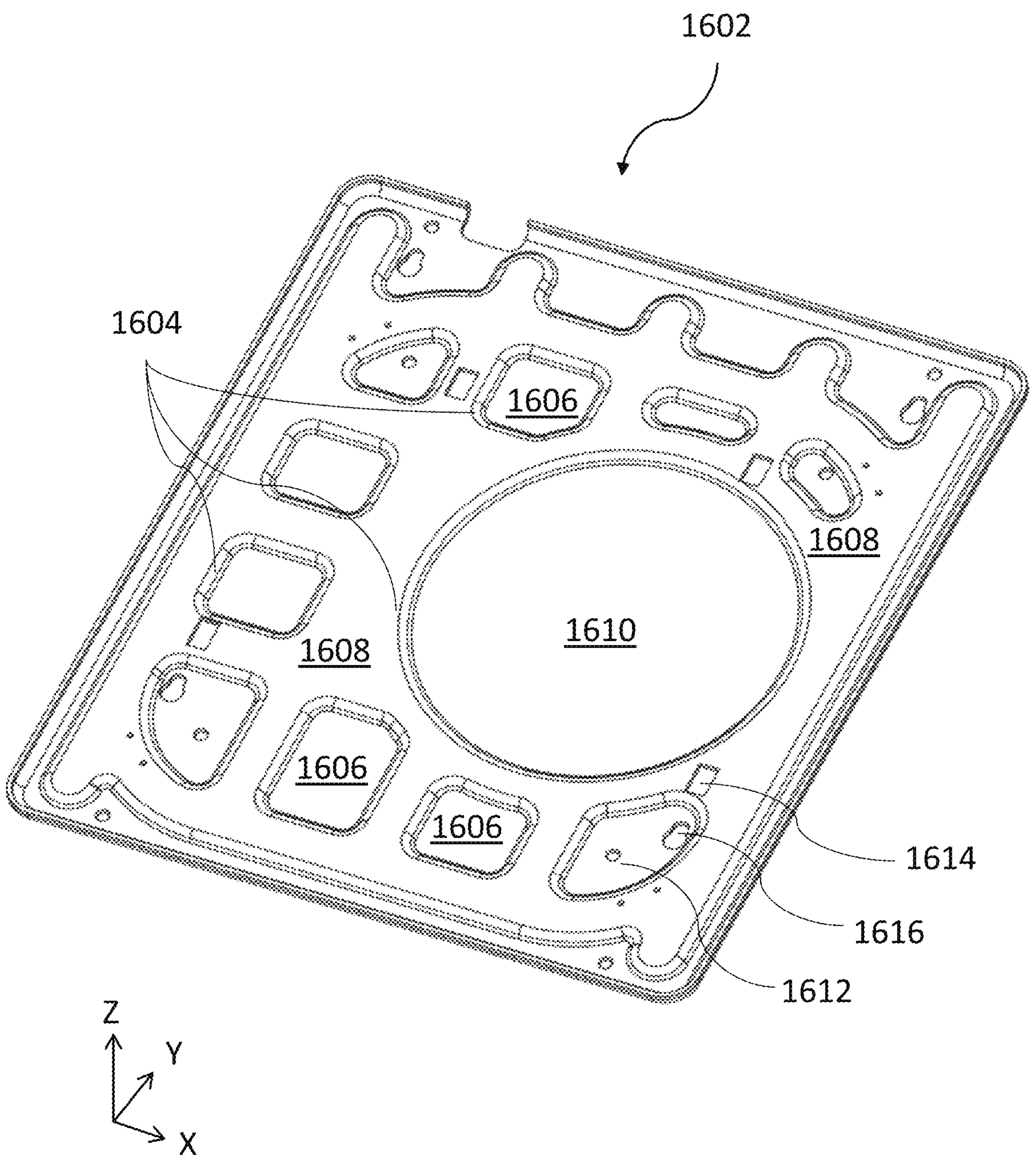
FIG. 16 illustrates a stiffening plate, according to an embodiment.
Figure 17:
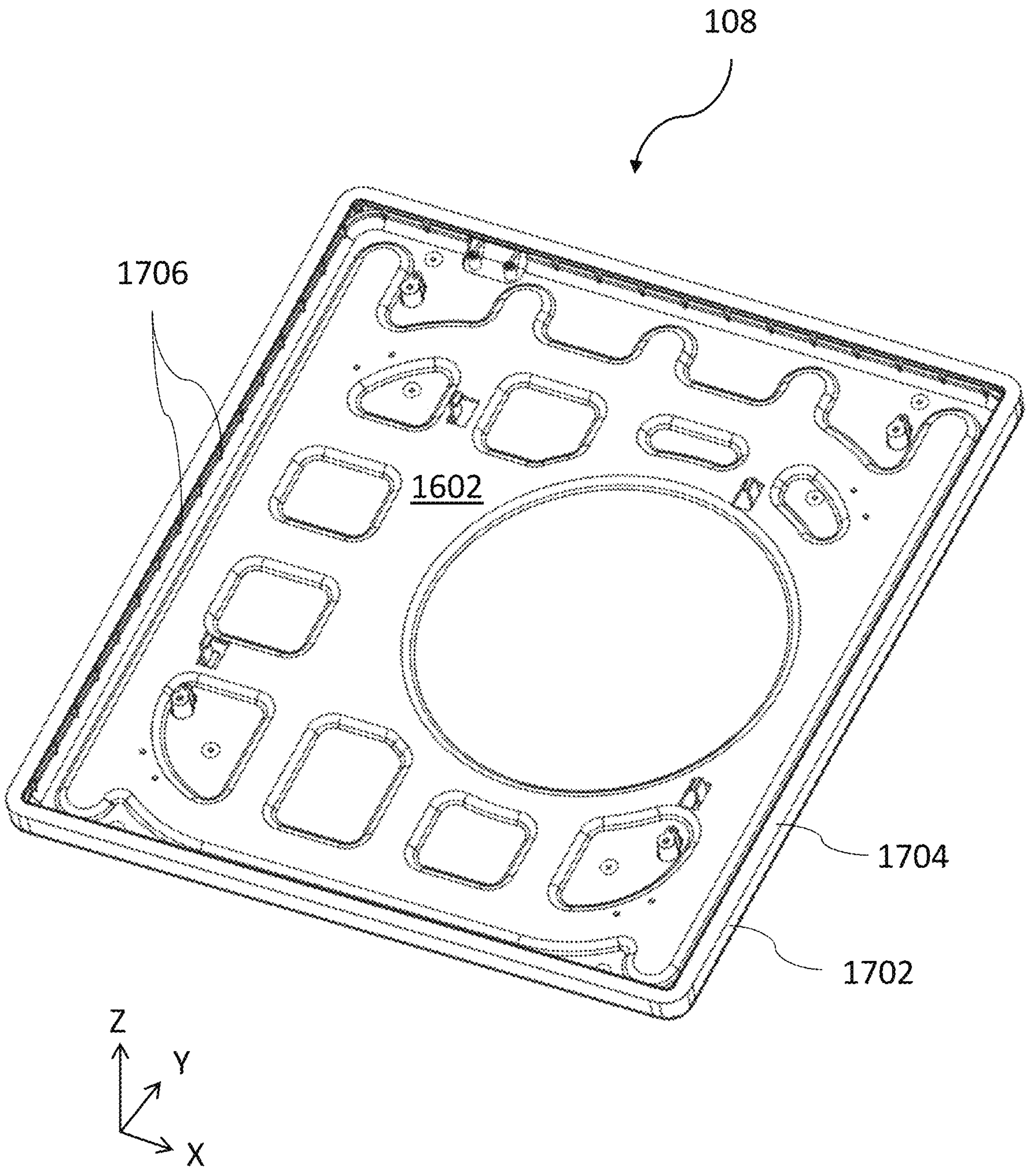
FIG. 17 illustrates a stiffening plate with a flange, according to an embodiment.

FIGS. 15 to 17 illustrate the base 108 or certain parts forming the base 108. In an embodiment, the base is a one-piece base (for example, made of metal to be sufficiently rigid).

However, such a base is heavy and expensive. To overcome these difficulties, the various functions of the base (structural support of the measurement station 100, aesthetic function, sealing function, function of securing the parts, weighing function, etc.), the base 108 may be made of several parts. In the embodiment illustrated in the figures, the base 108 comprises at least a frame 1508 and a stiffening plate 1602.

The stiffening plate 1602, which extends in an XY plane, is disposed between the frame 1508 (or within an open volume defined by the latter) and the support plate 202. The load cells rest directly on the stiffening plate 1602, which then provides the rigidity necessary to have a correct weight measurement, even on a soft (e.g., carpet) or non-planar (e.g., old parquet) floor. The stiffening plate 1602 may be made of metal, for example steel or aluminum. Aluminum has the benefit of being light. As illustrated in FIG. 16, the stiffening plate 1602 has ribs 1604 allowing, for the same amount of material, to increase the rigidity of the plate. The ribs 1604 are extensions along the plate Z direction. For example, the stiffening plate 1602 may be divided into at least two planar areas 1606, 1608 offset from each other along the Z direction and connected to each other by the ribs 1604. The planar areas 1606, 1608 further allow for the definition of indentations for housing the components of the measurement station. For example, the reel 802 that fit into the circular indentation 1610 in FIG. 16. The thickness of the stiffening plate 1602 (with ribs) may be between 5 mm and 15 mm, limits included, for example 10 mm. The thickness of the material may be between 0.5 mm and 2 mm, limits included, for example 1 mm.

The geometry of the ribs and thus the flat areas 1606, 1608 depends on at least two factors: the mechanical stress factor and the space factor. The ribs may be arranged in a grid pattern, maximizing the vertical (Z) portions that are resistant to bending, while leaving sufficient space in the Z to accommodate the components (particularly the reel 802)

The frame 1508 may be a single piece or may be formed from a plurality of parts. It has an aesthetic function (as a housing that hides the internal components of the measurement station 100) and may have a function of securing the parts together. For example, the frame 1508 is made of plastic (a lightweight material). As illustrated in FIGS. 15 and 17, the frame 1508 includes a bottom 1510 (extending substantially in the XY plane) and a sidewall 1702 (extending substantially along the Z direction from the edge of the frame 1508). The tab 1504 may extend from the frame 1508 (the bottom 1510 in particular). The tab 1504 then passes through a corresponding hole 1614 in the stiffening plate 1602. Alternatively, the fastener holes 1502 may be mounted to the frame 1508, for example, by being mounted to a spacer 1512 that extends along the Z direction from the bottom 1510. The spacer 1512 passes through a hole 1616 in the stiffening plate to contact the island 808 for assembly.

The elements 1514 of frame 1508 are temperature welding studs (shown in the melted position). In practice, they take the form of a plastic rod that is inserted into a corresponding through hole 1612 in the stiffening plate 1602, and then an operator or machine melts the end of the rod that spreads out and holds the stiffening plate 1602 and the frame 1508 together (bolting). Alternatively, screws may be used.

As seen in FIG. 2, the edge of the support plate 202 is recessed in X and Y direction from the edge of the base 108. As a result, the interior of the support station 100 could be visible. To avoid this, the sidewall 1702 may include a flange 1704, extending in a plane parallel to the XY plane from one end of the sidewall 1702 toward the interior of the base 108. To help hold the stiffening plate 1602, the side wall 1702 may include a plurality of clips 1706 that wedge (snap) the stiffening plate 1602 in place.

In an embodiment, the spacer 1512 is an independent part wedged between the frame 1508 (the bottom 1510 in particular) and the stiffening plate 1602. This makes it possible to manufacture the frame 1508 as a single piece by injection molding while allowing the injectors to move (otherwise the spacer blocks their passage).

Each stud 1514 is a thermal welding stud. It is a plastic part that is melted so that it changes its shape and locks the inserted part.

The frame 1508 may include the chamfer 204 that facilitates gripping the measurement station 100. The chamfer 204 is present between the bottom 1510 and the side wall 1702 and allows fingers to pass through.

The electronic circuitry of the load cells may be as described in PCT/FR2013/051754 or PCT/FR2021/050661.

As previously mentioned, the measurement station 100, and more particularly the base 102, may include a display 114 configured to display information to the user. The display 114 is attached to the support plate 202. The measurement plate 106 is positioned above the display 114. In an embodiment illustrated in FIGS. 8 and 9, the support plate 202 includes a housing 810 suitable for receiving the display 114. In order for the display 114 to be invisible when not powered and visible when powered, the measurement plate 106 is treated differently between an area facing the display 114 and the rest of the measurement plate 106.

In an embodiment, the sensors 104 include electrically conductive paths 602 (referred to as "electrodes") on the base 102 (see in particular FIGS. 6 and 7). The electrodes 602 may take the form of a metallic deposit on an upper surface 1104 of the measurement plate 106. The upper surface 1104 of the measurement plate 106 is defined as the surface receiving the user's feet (the visible surface). The upper surface 1104 is flat. To provide electrical connection to the PCB, the electrodes 602 pass through an edge of the measurement plate 106 and extend to a bottom surface 1204 of the measurement plate 106. The edge of the measurement plate 106 may have a rounded shape to ensure that the metal deposition is properly completed and electrical continuity is ensured. In addition, a rounded edge helps to avoid the risk of injury when gripping the measurement station 100. By rounded edge is meant a circular arc or similar shapes. The rounded edge also simplifies the metal deposition during manufacturing. Application FR2106653, incorporated by reference, describes these electrically conductive paths in detail.

The electrodes 602 are connected to the PCB via an electrical connector, which provides a connection between the electrically conductive path on the bottom surface 1204 and the PCB mounted on the support plate 202. The switch 566 allows the electrodes to be connected and disconnected to the various systems (ECG acquisition system, impedance measurement system, ESC system, etc.). In this way, each electrode may have several different functions depending on the switching position of the switch 566. For example, the switch 566 includes a plurality of switches controlled by the MCU.

Figure 11:
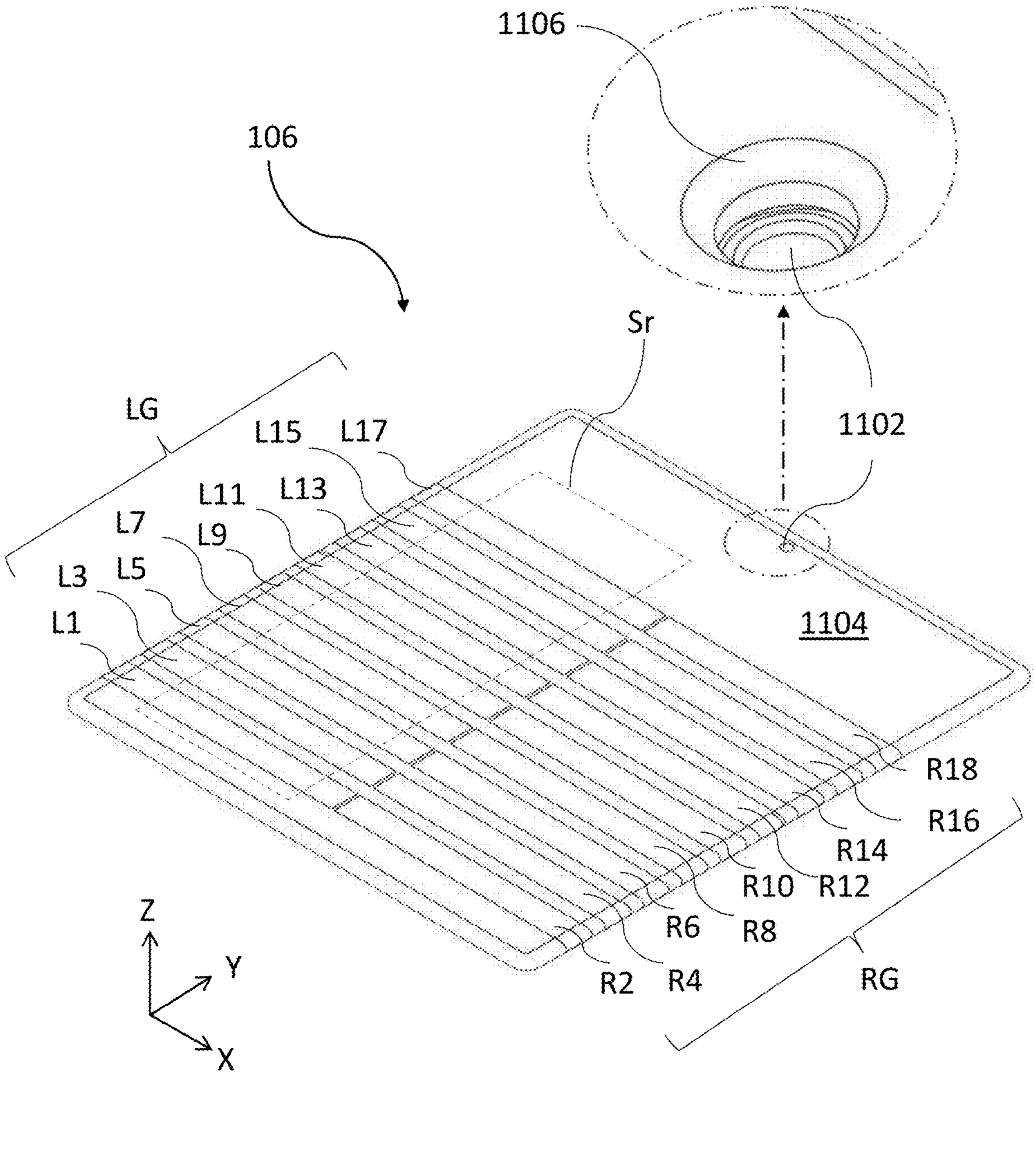
FIG. 11 illustrates a three-dimensional view of a measurement plate, with an enlargement, according to an embodiment.
Figure 12:
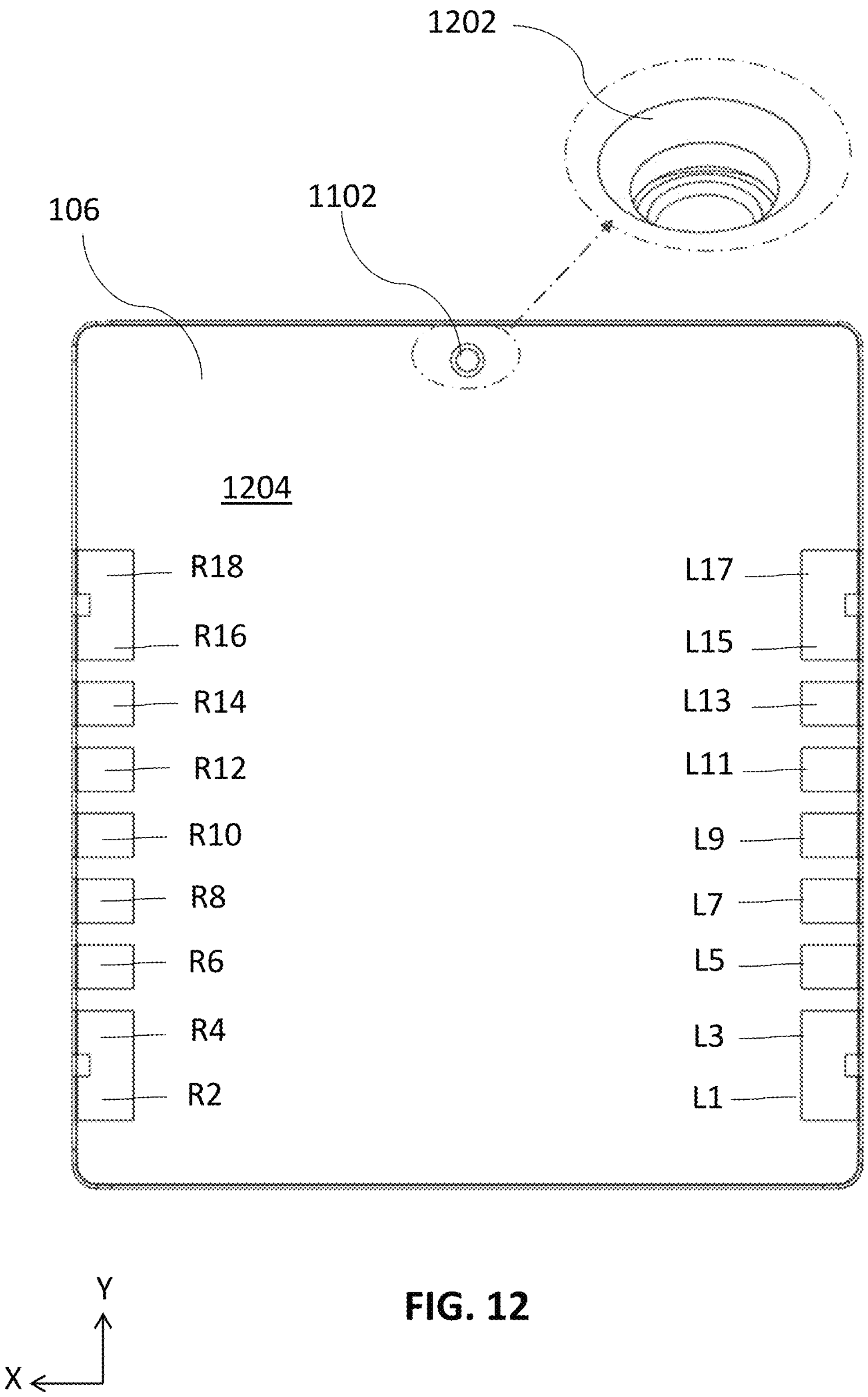
FIG. 12 illustrates a back view of a measurement plate, according to an embodiment.
Figure 13:
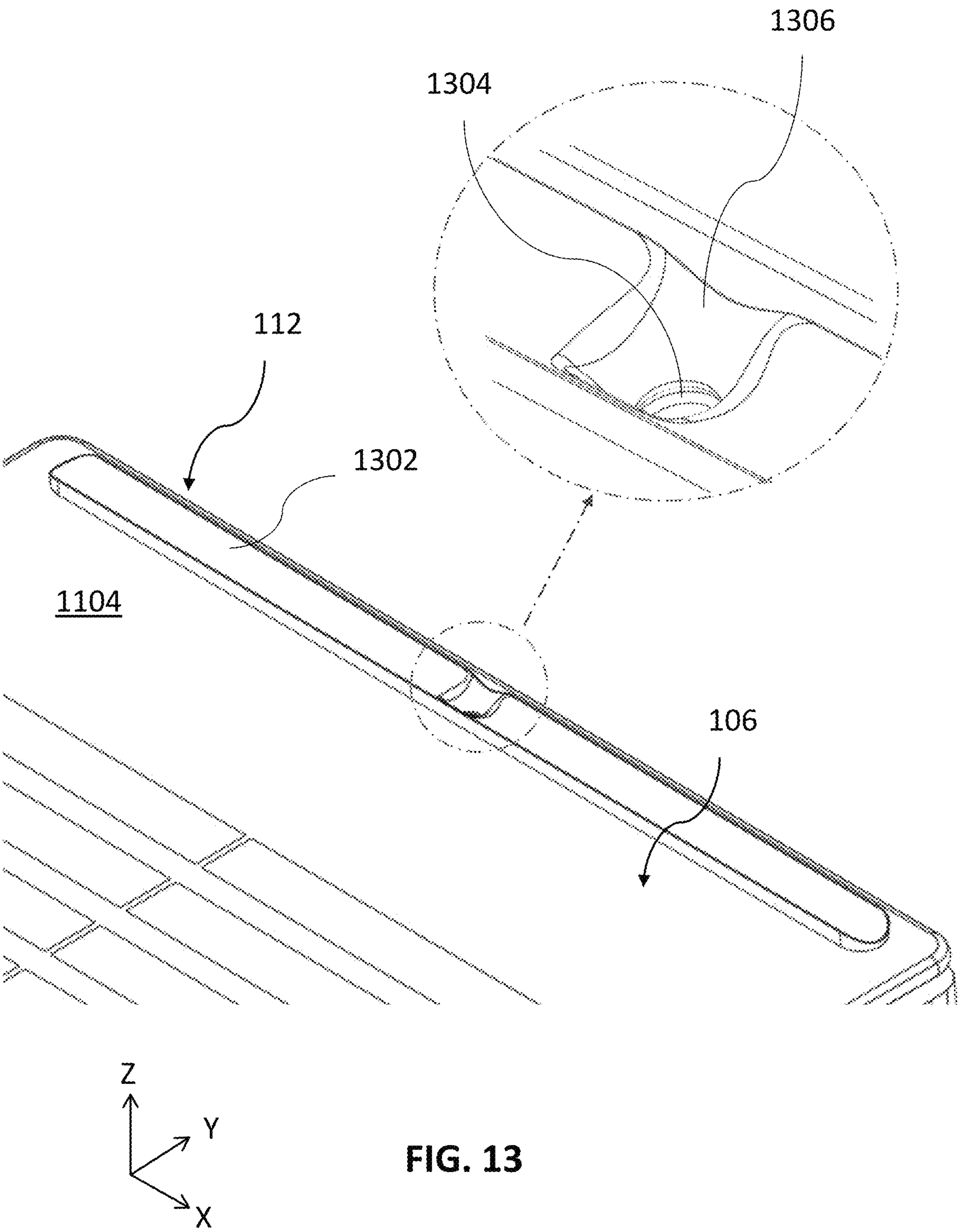
FIG. 13 illustrates a handle support with an enlargement, according to an embodiment.

The upper surface 1104 of the base 102 includes a left group LG of electrodes (intended to be in contact with the left foot, and a right group RG of electrodes intended to be in contact with the right foot. When the base 102 is set down in normal use, the user places his feet on a left side of the scale and a right side of the scale (with the toes on the display side 114). FIGS. 10 and 11 show electrically conductive paths L1, L3, L5, L7, L9, L11, L13, L15, L17 which form the electrodes of the left group LG of electrodes and electrically conductive paths R2, R4, R6, R8, R10, R12, R14, R16, R18, which form the electrodes of the right group RG of electrodes.

The electrodes on the base 102 may take the form of strips parallel to each other along the X direction (along the width of the base 102).

In the illustrated architecture, the pairs of paths L1 and L3; L15 and L17; R2 and R4; R16 and R18 are not independent but are permanently electrically connected, so that the base 102 includes in practice seven independent electrodes in the left group LG and seven independent electrodes in the right group RG. These permanent electrical connections may be made via the electrical paths on the measurement plate 106 (e.g., on the bottom surface 1204, not shown) or via the PCB of the measurement station 100.

In an example, the electrically conductive paths of the upper surface 1104 corresponding to the electrodes 1301-1312 have a dimension (on the upper surface 1104) along the length Y of between 1.5 cm and 2 cm, limits included, (e.g., 1.7 cm); the spacing between two successive strips may be between 0.5 cm and 1 cm, limits included, (e.g., 0.85 cm); the electrodes may have a dimension along the width X of greater than 10 cm. In particular, each group LG, RG may comprise at least four independent electrodes to in particular be able to perform an IPG in the foot (two electrodes connected to the AC source 560 and two electrodes connected to the voltmeter 562). In another embodiment, each LR, RG group may include at least two independent electrodes (to perform an ESC with anode/cathode and a high impedance electrode, or to perform a BIA or IPG between the legs), or three independent electrodes.

Figure 18:
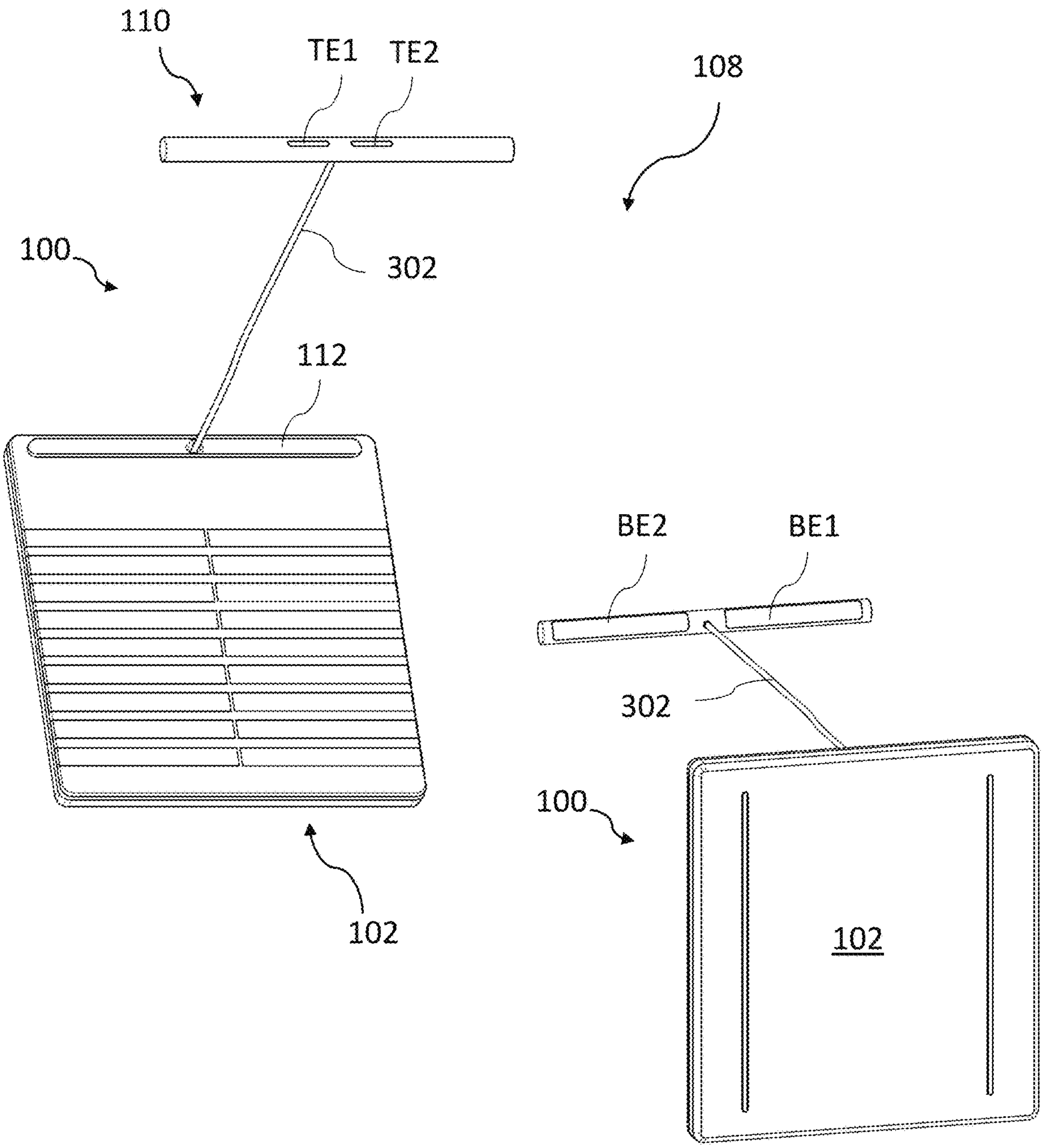
FIG. 18 illustrates another embodiment for the electrodes of the handle.

FIG. 18 illustrates another embodiment of the handle. In this embodiment, the handle 110 includes two back electrodes BE1 (for the left hand, the palm more precisely), BE2 (the right hand, the palm more precisely), for which the angular considerations of the handle electrodes RH1, RH2, LH1, LH2 as previously disclosed apply. The handle 110 further includes two top electrodes TE1, TE2 configured to receive the thumbs (of respectively the left hand and the right hand) and located on top of the handle. In terms of function, electrodes TE1 and TE2 may correspond to electrodes RH2 and LH2 and electrodes BE1, BE2 may correspond to RH1 and LH1.

The top electrodes TE1, TE2 are located opposite of the cable 302 on the handle 110, in a symmetrical manner of a median plane (which includes the location where the cable 302 enters the handle 110). The top electrodes TE1, TE2 are located around 180° (using the definition of the angles previously given), such as between 175° and 185°, limits included, (or between −175 and −185°, limits included). The dimensions of the top electrodes TE1, TE2 are much smaller than the back electrodes BE1, BE2, as they are designed to be less visible and to only contact the thumbs. For example, their length along the X direction is less than 5 cm (for example between 3 cm and 5 cm, limits included) and their width along a periphery of the handle 110 is less than 1 cm (for example around 0.5 cm, limits included). Top electrodes TE1, TE2 may be between 1 and 4 cm, limits included, away from each other.

In an implementation, the top electrodes are made of conductive material of a similar color to the rest of the visible part of the handle 110, so that top electrodes TE1, TE2 are barely visible.

It will be appreciated that the various embodiments described previously are combinable according to any technically permissible combinations.

The invention claimed is:

1. A measurement station comprising:

a base comprising:

a measurement plate having an upper surface adapted to receive a user's feet, wherein the measurement plate comprises a flat glass plate having an outer periphery delimiting the flat glass plate, a handle support mounted on the upper surface of the flat glass plate, wherein the handle support is positioned within the outer periphery, a handle adapted to receive a user's hands, the handle being configured to be removably received on the handle support, wherein the handle is movable between (a) a stowed position in which the handle is supported on the handle support and is (i) located within the outer periphery and (ii) raised above the upper surface of the flat glass plate and (b) an extended position.

2. The measurement station according to claim 1, comprising a cable connecting the handle to the base.

3. The measurement station according to claim 2, wherein the measurement plate comprises a plate through hole, wherein the cable connecting the handle to the base passes through the plate through hole.

4. The measurement station according to claim 3, wherein the handle support comprises a support through hole, wherein the cable passes through the support through hole, and wherein the plate and support through-holes are opposite each other.

5. The measurement station according to claim 4, wherein the cable extends orthogonally from a surface of the handle, so as to be insertable without change of direction into the plate and support through holes when the handle is positioned in the handle support.

6. The measurement station according to claim 3, wherein the handle support comprises a support through hole, wherein the cable passes through the support through hole, and wherein the plate through-hole of the measurement plate and/or the support through-hole of the handle support has a chamfer.

7. The measurement station according to claim 2, wherein the handle support comprises a support through hole, wherein the cable passes through the support through hole.

8. The measurement station according to claim 2, wherein the base comprises a reel adapted to wind and unwind the cable.

9. The measurement station according to claim 8, wherein the base comprises a first roller configured to facilitate a change in direction of the cable during winding and unwinding of the cable.

10. The measurement station according to claim 9, wherein the base further comprises a second roller configured to channel the movement of the cable, the first and second rollers being on opposite sides of the cable.

11. The measurement station according to claim 1, wherein the handle support forms a cradle configured to receive the handle.

12. The measurement station according to claim 11, wherein the handle support comprises a support through hole, wherein the cable passes through the support through hole, and wherein the second through hole of the handle support is positioned at a bottom of the cradle.

13. The measurement station according to claim 11, wherein the cradle extends over an area, in a cross-section of the handle support, of less than 90° on either side from a bottom of the cradle.

14. The measurement station according to claim 1, wherein the handle extends between two ends and comprises a plurality of electrodes arranged in succession between the two ends.

15. The measurement station according to claim 14, comprising a cable connecting the handle to the base, wherein the electrodes extend, in an orthogonal section, at most over an outer surface of the handle from −45° to +90°, 0° being defined by an stowed position of the cable in the handle, a range from 0 to +180° being defined as facing a front edge of the measurement station.

16. The measurement station according to claim 15, wherein the handle support forms a cradle configured to receive the handle, and wherein the cradle extends over a surface whose angle in a cross-section of the handle support is at least equal to that of the plurality of electrodes in the negative angle direction, when the handle is in the stowed position.

17. The measurement station according to claim 14, wherein the handle is configured to allow acquisition of an electrocardiogram and an impedance analysis.

18. The measurement station according to claim 1, wherein the handle comprises two top electrodes located on top of the handle, wherein a length of each of the two top electrodes is less than 5 cm, a width of each of the two top electrodes is less than 1 cm and the two top electrodes are from 1 to 4 cm from each other.

19. The measurement station according to claim 18, wherein a color of the two top electrodes is similar to that of the rest of the handle.

20. The measurement station according to claim 1, further comprising a cable connecting the handle to the base, wherein the handle comprises a second through hole, and wherein the cable passes through the first and second through holes.

* * * * *